(12) United States Patent
Cuppens

(10) Patent No.: US 8,318,434 B2
(45) Date of Patent: Nov. 27, 2012

(54) METHOD FOR INTRODUCING A SAMPLE SPECIFIC DNA TAG INTO A PLURALITY OF DNA FRAGMENTS FROM A PLURALITY OF SAMPLES

(75) Inventor: Harry Cuppens, Brussel (BE)

(73) Assignee: Katholieke Universiteit Leuven, K.U.Leuven R&D, Leuven (BE)

( * ) Notice: Subject to any disclaimer, the term of this patent is extended or adjusted under 35 U.S.C. 154(b) by 271 days.

(21) Appl. No.: 12/728,071

(22) Filed: Mar. 19, 2010

(65) Prior Publication Data

US 2010/0227329 A1 Sep. 9, 2010

Related U.S. Application Data

(63) Continuation-in-part of application No. PCT/BE2008/000073, filed on Sep. 22, 2008.

(30) Foreign Application Priority Data

Sep. 21, 2007 (GB) .................................... 0718456.7
Dec. 21, 2007 (GB) .................................... 0724985.7

(51) Int. Cl.
*C12Q 1/68* (2006.01)
*C12P 19/34* (2006.01)
(52) U.S. Cl. ...................................... 435/6.12; 435/91.2
(58) Field of Classification Search ................. 435/6.12, 435/91.2
See application file for complete search history.

(56) References Cited

U.S. PATENT DOCUMENTS

| | | | |
|---|---|---|---|
| 6,027,889 A * | 2/2000 | Barany et al. ................ | 435/6.12 |
| 6,309,833 B1 | 10/2001 | Edman et al. | |
| 2003/0049629 A1 | 3/2003 | Edman et al. | |
| 2003/0148335 A1 | 8/2003 | Shen et al. | |
| 2004/0029165 A1 | 2/2004 | Wong | |
| 2005/0003380 A1 | 1/2005 | Cohen et al. | |

(Continued)

FOREIGN PATENT DOCUMENTS

WO   WO 00/61817 A1   10/2000

(Continued)

OTHER PUBLICATIONS

Andreadis et al., "Use of Immobilized PCR Primers to Generate Covalently Immobilized DNAs for in vitro Transcription/Translation Reactions," *Nucleic Acids Research* 28(2):e5, 2000.

(Continued)

*Primary Examiner* — Kenneth R. Horlick
(74) *Attorney, Agent, or Firm* — Clark & Elbing LLP

(57) ABSTRACT

The invention discloses methods for introducing a sample specific DNA tag into a plurality of DNA fragments from a plurality of samples. For each of the samples, the method involves (1) amplifying DNA fragments in a first multiplex or multiplex-like PCR reaction using amplicon specific forward and reverse primers. Each forward amplicon specific primer including a first adaptor sequence and each reverse amplicon specific primer including a second adaptor. The first adaptor sequence is identical in all forward primers for each of the samples. The second adaptor sequence is identical in all reverse primers for each of the samples, and (2) further amplifying the amplified nucleic acids obtained using one set of forward and reverse sample specific primers which are directed against the first and second adaptor sequences. One or both of the sample specific primers includes a DNA sequence which differs for each of the samples.

11 Claims, 17 Drawing Sheets

U.S. PATENT DOCUMENTS

| | | |
|---|---|---|
| 2005/0170373 A1* | 8/2005 | Monforte .................. 435/6 |
| 2005/0196760 A1 | 9/2005 | Pemov et al. |
| 2007/0003950 A1 | 1/2007 | Shen et al. |
| 2007/0128624 A1 | 6/2007 | Gormley et al. |
| 2008/0051294 A1 | 2/2008 | Gormley et al. |
| 2009/0117621 A1 | 5/2009 | Boutell et al. |

FOREIGN PATENT DOCUMENTS

| | | |
|---|---|---|
| WO | WO 02/064835 A2 | 8/2002 |
| WO | WO 02/103011 A2 | 12/2002 |
| WO | WO 2005/042759 A2 | 5/2005 |
| WO | WO 2005/068656 A1 | 7/2005 |
| WO | WO 2007/010254 A1 | 1/2007 |
| WO | WO 2007/052006 A1 | 5/2007 |
| WO | WO 2007/060456 A1 | 5/2007 |
| WO | WO 2007/081386 A2 | 7/2007 |
| WO | WO 2007/081387 A1 | 7/2007 |
| WO | WO 2009/036525 A2 | 3/2009 |

OTHER PUBLICATIONS

Brownie et al., "The Elimination of Primer-Dimer Accumulation in PCR," *Nucleic Acids Research* 25:3235-3241, 1997.

Hamady et al., "Error-Correcting Barcoded Primers for Pyrosequencing Hundreds of Samples in Multiplex," *Nature* 5:235-237, 2008. (35 pages of Supplementary Material).

Margulies et al., "Genome Sequencing in Microfabricated High-Density Picolitre Reactors," *Nature* 437:376-380, 2005. (Erratum: published *Nature* 441:120, 2006).

Meuzelaar et al., "MegaPlex PCR: A Strategy for Multiplex Amplification," *Nature Methods* 4:835-837, 2007.

Tucker et al., "Massive Parallel Sequencing: The Next Big Thing in Genetic Medicine," *The American Journal of Human Genetics* 85:142-154, 2009.

Search Report and Written Opinion (Form PCT/ISA/220) for International Application No. PCT/BE2008/000073, mailed Jul. 21, 2009.

Reply to Written Opinion for International Application No. PCT/BE2008/000073 (Jul. 21, 2009), dated Oct. 22, 2009.

International Preliminary Report on Patentability for International Application No. PCT/BE2008/000073, completed Mar. 5, 2010.

Official Communication from European Patent Office for European Patent Application No. 08 800 182.1, dated Nov. 30, 2010.

Official Communication and Annex for European Patent Application No. 08 800 182.1, dated Dec. 14, 2011.

\* cited by examiner

| 25nt-random-plasmids | | Unique sample-ID-barcodes |
|---|---|---|
| Number | Total number | |
| 1 set | 10 | 10 | 10 |
| 3 sets | 10 | 30 | 1000 |
| 6 sets | 10 | 60 | 1 million |

Figure 11

No error:

| 1A | 2A | 3A | 4A | ... | 100A |
| ST1 | ST2 | ST3 | ST4 | ... | ST100 |

- Uneven switch : detected
  e.g. 2A ↔ 1A
  ST1   ST2

- Double switch : detected,
  e.g. 2A ↔ 1A
  ST3        ↔ ST1 except reciprocal switch
  e.g. 2A ↔ 5A    in 100 samples
  ST2 ↔ ST5

$$P = \frac{1}{99 * 99 * 99 * 99} \sim 1/10^8$$

SEQUENCE LISTING

<160> NUMBER OF SEQ ID NOS: 1

<210> SEQ ID NO 1
<211> LENGTH: 34
<212> TYPE: DNA
<213> ORGANISM: artificial sequence
<220> FEATURE:
<223> OTHER INFORMATION: biotinylated tag
<220> FEATURE:
<221> NAME/KEY: misc_feature
<222> LOCATION: (1)..(1)
<223> OTHER INFORMATION: biotinylated
<220> FEATURE:
<221> NAME/KEY: misc_feature
<222> LOCATION: (34)..(34)
<223> OTHER INFORMATION: biotinylated

<400> SEQUENCE: 1
ccgttaaccc gatatcggcc cgggccttta aacc         34

METHOD FOR INTRODUCING A SAMPLE SPECIFIC DNA TAG INTO A PLURALITY OF DNA FRAGMENTS FROM A PLURALITY OF SAMPLES

CROSS REFERENCE TO RELATED APPLICATIONS

This application is a continuation-in-part of International Application No. PCT/BE2008/000073, filed on Sep. 22, 2008, which was published in English under PCT Article 21(2), and which claims the benefit of UK patent application GB0718456.7, filed on Sep. 21, 2007, the disclosures of which are incorporated by reference in their entirety. This application also claims the benefit of UK patent application GB0724985.7 filed on Dec. 21, 2007, the disclosure of which is incorporated by reference in its entirety.

FIELD OF THE INVENTION

The present invention relates to tools and methods for use in genetic tests involving high performance sequencing techniques. More particularly, the invention relates to a robust multiplex PCR method wherein the respective primers for amplifying the different amplicons are physically isolated from one another. The invention further relates to quality control methods allowing a stringent quality control of genetic tests carried out according to the present invention.

BACKGROUND OF THE INVENTION

Mutations/variations in the human genome are involved in most diseases, going from monogenetic to multifactorial diseases, and acquired diseases such as cancer. Even the susceptibility to infectious diseases, and the response to pharmaceutical drugs, is affected by the composition of an individual's genome. Most genetic tests, which screen for such mutations/variations, require amplification of the DNA region under investigation. However, the size of the genomic DNA that can be amplified is rather limited. For example, the upper size limit of an amplified DNA fragment in a standard PCR reaction is about 2 kb. This contrasts sharply with the total size of 3 billion nucleotides of which the human genome is build up. As more and more mutations/variations are found to be involved in disease, there is a need for robust assays in which different DNA regions, that harbor the different mutations/variations, are analyzed together. This may be achieved through (more complex) multiplex amplification reactions.

In this application, PCR is the method of amplification of DNA that is mainly described, however the embodiment of this invention may be used for any amplification technique known to the art, such as isothermal amplification (rolling circle amplification), ligase chain reaction, nucleic acid sequence-based amplification (NASBA), padlock probes, single strand displacement amplification, and whole genome amplification.

In a classical multiplex PCR reaction, different fragments are amplified in a single tube, simply by adding all pairs of amplicon-specific primers to a reaction mixture. The higher the number of primers that are combined in a single PCR reaction, the higher the chance that particular primer interactions (such as primer-dimerization), and aspecific primer/template interactions occur, so that particular amplicons fail to amplify. There is thus a limitation in the number of amplicons that can be co-amplified when primers are simply mixed. Certain primer combinations work in one multiplex reaction, but not in another multiplex reaction. Also the amount of primers that are added may affect the success of a multiplex PCR amplification. The determination of amplicons that can be co-amplified, and the development of a robust multiplex PCR reaction of these amplicons, needs to be determined empirically by trial and error and is rather time-consuming. Each multiplex PCR reaction needs its own optimization. In a robust multiplex PCR reaction, 5-15 amplicons can be combined. A higher number of amplicons may be multiplexed, however at the expense of the robustness of the assay which affects the success rate of a multiplex amplification.

Robust multiplex PCR reactions of a large number of amplicons may be achieved when the different primers are physically restricted. Here we propose different methods to trap molecular components allowing a physically restricted amplification with minimal interference of other molecular components.

New sequencing techniques allow a very large throughput and the generation of large amounts of data. They may even generate much more sequence data than needed for the analysis of one sample. In order to make full use of the capacity of a technique, and therefore at an economical cost, different samples need to be pooled in one single sequencing run. This requires that the origin of the DNA fragments derived from the respective samples can be traced. Addition of a DNA-tag to a DNA fragment of a sample that one wants to analyze can be obtained in a one step amplification process in which at least one amplicon-specific primer contains the tag as an adaptor. However, this will be still very costly since the number of primers will increase very rapidly with increasing number of samples and increasing number of amplicons to be analyzed per sample.

Prior Art:

SUMMARY OF THE INVENTION

The new generation sequencing technology, such as parallel pyrosequencing in high-density picoliter reactors, allows the simultaneous sequencing of extreme high numbers of 25-500 bp fragments and is currently mainly used for total genomic sequencing. The present invention is based on the finding that when using adapted sample preparation methods and protocols these sequencing technologies can also be used in other sequencing applications such as the resequencing of specific nucleic acid fragments in biological samples, as used in clinical diagnostics. In a first instance, it was found that a successful use of the sequencing technologies preferably requires the availability of robust multiplex PCR reactions of a large number of amplicons. Therefore, it is a first object of the present invention to provide tools and methods for carrying out robust multiplex PCR reactions wherein the respective primers for amplifying the different amplicons are physically isolated from one another. This is achieved through the use of molecular complexes (hereinafter also referred to as DNA KNEX crystals) comprising two or more linked nucleic acids or analogues thereof wherein the molecular complexes comprise at least one forward primer and at least one reverse primer suitable for the PCR amplification of a given nucleic acid fragment. Preferably, the molecular complexes are soluble in an aqueous solution.

In a preferred embodiment, a molecular complex according to the present invention comprises one or more core molecules, which comprise a nucleic acid or a plurality of linked nucleic acids or analogues, for instance via avidin-streptavidin/biotin interactions. The core molecules further comprise at least two binding sites linking the core molecule to other core molecules and/or to functional molecules, which are nucleic acids or analogues thereof comprising either of the PCR primers. In a more preferred embodiment, the binding sites in the core molecule are two or more biotin molecules, while the functional molecules comprise at least one biotin molecule (FIG. 1). This allows to firmly link the respective core and functional molecules using avidin or streptavidin as a linker molecule.

The molecular complexes according to the present invention can also be used after immobilisation on a support, for instance on a support coated with avidin or streptavidin, which allows for binding the molecular complex through interaction with free biotin molecules in the molecular complex. Preferably, the support is the wall of a reaction vessel, such as a test tube.

In a second object, the present invention provides a method for carrying out PCR amplification of a DNA fragment the method comprising the use of molecular complexes according to the present invention wherein each of the complexes comprise one or more forward primers and one or more reverse primers allowing the amplification of the DNA fragment (FIG. 2). More preferably, the PCR method is a multiplex PCR for the simultaneous amplification of different DNA fragments wherein multiple sets of molecular complexes are used (FIG. 3). The respective sets of molecular complexes each comprise complexes comprising one or more forward primers and one or more reverse primers specific for the amplification of one of the multiple DNA fragments to be amplified. The PCR method of the present invention is of particular interest for the amplification of a genomic DNA fragment or set of fragments for the purpose of sequencing a section of the genomic DNA.

New sequencing techniques allow a very large throughput and the generation of large amounts of data. They may even generate much more sequence data than needed for the analysis of one sample. In order to make full use of the capacity of a technique, and therefore at an economical cost, different samples need to be pooled in one single sequencing run. This requires that the origin of the DNA fragments derived from the respective samples can be traced. This can for instance be achieved by incorporating a same DNA tag in all DNA fragments derived from a given sample. The sequencing of these DNA fragments, including the incorporated tags, subsequently allows to analyze the parts of the fragments to be investigated as well as to determine the origin of the respective fragments.

Therefore, in a third object, the present invention provides a method for introducing a DNA tag into a DNA fragment (FIG. 4a), including cDNA fragments, derived from a sample comprising genetic material. Herein the DNA tag is identical for all DNA fragments of a sample. The method is typically performed on a plurality of samples and the method comprising for each of the samples the steps of:
  i. the amplification of a first DNA fragment in a first PCR-reaction using a first set of amplicon specific forward and reverse primers, each of the primers comprising an adaptor, preferably a first adaptor for the forward primer and another second adaptor for the reverse primer. Herein the first adaptor sequence is the same for all forward primers in a sample and the second adaptor sequence is the same for all reverse primers in a sample. Within one sample the first and second adaptor sequence can be the same but typically differ from each other
  ii. subsequently amplifying the first DNA fragment in a second PCR reaction using a second set of primers, called sample specific primers directed against the adaptor sequences, wherein either or both of the second set of primers comprises a DNA-tag. One pair of primers allows to amplify all fragments obtained in (i) in one sample, because of the adaptor sequences that have been introduced in step (i). These adaptor sequences serve as template for the sample specific primers.

Typically the method is performed on samples which each comprise more than one DNA fragment. In a more preferred embodiment, a same sample specific tag is introduced in more than one DNA fragment derived from a sample.

In a particular embodiment, the first set of amplicon specific primers of step (i) are comprised in a molecular complex according to the first object of the present invention (FIG. 4b). In this case the amplification of the first set of DNA fragments involves the use of a method according to the second object of the present invention.

Preferably either or both of the second set of primers used in step (ii) comprises an additional adaptor for further processing purposes. Typically the additional adaptor is a further oligonucleotide sequence which is used for example for hybridization to beads or arrays.

The introduced DNA tag is a known nucleic acid sequence, more preferably the DNA tag comprises one or more primary tags wherein each primary tag comprises a known sequence. The DNA tag may comprise a repetition of a same primary tag.

When the relation between each of the introduced DNA tags and the samples from which the DNA fragments are derived is documented, it becomes possible to identify from which sample a DNA fragment is derived based on its sequence in as far a unique same DNA tag was introduced in all DNA fragments derived from a same sample. In a more preferred embodiment, the information on the relation between each of the introduced DNA tags and the samples from which the DNA fragments are derived together with the determination of the sequences of the fragments allows to automatically report the results of the sequence analysis for each of the samples.

Finally it was found that the quality control of diagnostic procedures involving a biological sample, particularly when the analysis of the sample comprises the sequencing of nucleic acid fragments comprised in the sample, can be significantly improved by adding one or more nucleic acids comprising a known sequence to that sample prior to its analytic processing. Retrieval of the known sequences at the end of the analytical process will allow to verify the origin of the sample. Therefore, in a fourth object, the present invention provides a method for marking and subsequently verifying the origin and/or identity of a biological sample the method comprising the steps of:
  i. providing an isolated biological sample;
  ii. adding to the sample one or more marker nucleic acids (for example plasmids), each such marker nucleic acid comprising a known nucleic acid sequence, the known sequence being unique for each of the added marker nucleic acids. However, in case more than one marker nucleic acids are added, at least one should be different;
  iii. documenting the relation between the identity and/or origin of the biological sample and the addition of the one or more marker nucleic acids to the sample;
  iv. detecting the presence in the biological sample the known nucleic acid sequences comprised in the marker nucleic acids; and
  v. verifying whether the sequences detected in step (iv) are in accordance with the documentation obtained in step (iii) in order to verify the identity and/or origin of the biological sample.

Preferably, the presence in the biological sample of the known nucleic acid sequences is detected by PCR amplification of the sequences and subsequently sequencing the amplification products.

The method according to the present invention is particularly useful in the quality control of the sequencing of nucleic acid fragments comprised in a biological sample. Preferably, the known sequences comprised in the marker nucleic acids are processed in the same way as the DNA fragments of the sample. In a particular embodiment this implies that in the DNA fragments obtained by PCR amplification of the known nucleic sequences of the added marker nucleic acids and in the DNA fragments obtained by PCR amplification of the nucleic acid sequences to be characterized by sequencing a same DNA tag is simultaneously incorporated (FIGS. 5a and 5b). The anticipated presence of the DNA tag in the DNA fragments derived from the sample and in the DNA fragments comprising the known sequences derived from the marker nucleic acids allows for a very stringent quality control of both the origin and the processing of the samples. In a more preferred embodiment the detection of the introduced DNA tag and that of the known nucleic acid sequences are used in the automatic reporting on the results of the analysis of the DNA fragments derived from the biological samples.

In yet another preferred embodiment, the marker nucleic acids are already present in the vessel (e.g. a collector tube) in which the sample is collected. The present invention also provides a vessel or collector tube wherein one or more marker nucleic acids are present, each such marker nucleic acid comprising a known nucleic acid sequence, the known sequence being unique for each of the added marker nucleic acids. However, in case more than one marker nucleic acids are added, at least one should be different, so that the set or combination of marker nucleic acids are unique for each sample.

In summary, one aspect of the invention relates to a method for introducing a sample specific DNA tag into a plurality of DNA fragments from a plurality of samples comprising genetic material. The method comprises, for each of the samples, the steps of:
(i) amplifying DNA fragments in a first multiplex or multiplex-like PCR-reaction using amplicon specific forward and reverse primers, wherein each forward amplicon specific primer comprises a first adaptor sequence and wherein each reverse amplicon specific primer comprises a second adaptor, wherein the first adaptor sequence is identical in all forward primers for each of the samples and wherein the second adaptor sequence is identical in all forward primers for each of the samples,
(ii) further amplifying the amplified nucleic acids obtained in step i, using one set of forward and reverse sample specific primers which are directed against the first and second adaptor sequences, wherein one or both of the sample specific primers comprises a DNA sequence which differs for each of the samples.

According to particular embodiments, one or both of the second set of primers comprise one or more additional different adaptors further processing purposes. According to other particular embodiments the amplicon specific primers used in steps (i) and the sample specific primers (ii) are added together in one reaction mixture.

According to other particular embodiments, the amplicon specific primers and the sample specific primers have specific different melting temperatures allowing selective amplification by modifying the annealing temperature. Herein the amplicon specific primers are designed to have an annealing temperature which resides in a low temperature range, and the sample specific primers are designed to have an annealing temperature which is significantly higher than the amplicon specific primers. Consequently, at lower temperatures, the amplication with all primers will occur. When after a number of cycles, the annealing temperature is elevated, the amplicon specific primers will not anneal anymore, and only the sample specific primer will anneal.

According to further embodiments, methods of the present invention may comprise the additional steps of:
(iii) determining for an amplified DNA fragment obtained in step ii the nucleic acid sequence of the sample specific DNA tag and the nucleic acid sequence of the DNA fragment, and
(iv) correlating the sequence information of the DNA fragment with the sample from which the DNA fragment is derived. Optionally, nucleic acids are pooled prior to determining the nucleic acid sequence of the amplified nucleic acids.

According to other embodiments, methods of the present invention may comprise the additional step of, prior to step (i), the step of adding to each sample one or a combination of different marker nucleic acids, with a known nucleic acid sequence, wherein for each sample, the marker nucleic acid, or the combination of different marker nucleic acid is unique, and wherein the marker sequence or sequences are amplified with amplicon specific markers and sample specific markers in accordance with step (i) and (ii).

According to other embodiments, methods of the present invention may comprise the additional step of, after amplification of a marker nucleic acid, determining the sequence of the sample specific DNA tag and the sample specific DNA marker sequence in the amplified DNA marker nucleic acid.

According to other embodiments of methods of the present invention, each of the different nucleic acids in a combination of marker nucleic acids comprises a randomly generated molecular bar code region and wherein each of the different nucleic acids comprises 5' and/or 3' of the randomly generated molecular bar code region an adapter sequence which is identical for each of the different marker nucleic acids and which is able to anneal with a primer allowing for the amplification of the molecular bar code region.

According to other embodiments of methods of the present invention the added marker nucleic acids are designed so that they can be processed together or in parallel in the same strategy as the nucleic acid sequences of the biological sample under investigation.

According to other embodiments of methods of the present invention the one or more marker nucleic acids are present in a collector tube prior to the administration of a sample.

According to other embodiments of methods of the present invention either or both the detection of the introduced DNA tag and that of the known nucleic acid sequences are used in the automatic reporting on the results of the analysis of the DNA fragments derived from the biological samples.

Another aspect of the present invention relates to a set of tubes with DNA in a dried form wherein each tube comprises:
 a label on the wall or the lid of the tube and
 marker nucleic acid or a combination of different marker nucleic acids, wherein for each tube, the marker nucleic acid, or the combination of different marker nucleic acid is unique,
 a pair of primers which hybridizes to the one marker nucleic acid or to each in the combination of different marker nucleic acids, wherein the set of primers is identical for all tubes in the set.

Typically the marker nucleic acid is a plasmid, a fragment of a plasmid or an oligonucleotide with the length of between 30 and 65 nucleotides.

A first marker nucleotide sequence comprises a unique sequence, compared to a second or further markers sequence. The marker sequences can be stretches between 5 and 30 nucleotides, allowing a complexity from $4^5$ to $4^{30}$ combinations.

Typically the unique part of the marker sequence is flanked by sequences which are common for all marker sequences, typically sequences of at least 13 nucleotides which act as templates in a PCT amplification step.

In the above described set of tubes, the identity of the marker sequence is indicated by a label on the tube, which can be a alphanumeric indication, a bar code or another graphical display.

DETAILED DESCRIPTION OF THE INVENTION

Legends to the Figures

FIG. 1 shows a schematic representation of KNEX-DNA-crystals.

Panel A. KNEX-DNA-crystal is build up of biotinylated oligonucleotides, the core-oligonucleotide contains 3 biotin moieties, the functional oligonucleotides contain 1 biotin moiety. Here, two functional oligonucleotides contain a 3' amplicon-specific domain which will allow amplification of the respective amplicon, and an adapter domain which will be used as priming site in another polymerization/amplification process. Streptavidin is used for cross-linking all oligonucleotides.

Panel B. Crosslinking of the core-oligonucleotides and streptavidin allows the formation of a complex core-network.

Panel C. Crosslinking of the core-oligonucleotides and functional oligonucleotides allow the formation of amplicon-specific KNEX-DNA-crystals.

FIG. 2 shows the principle of local amplification at an amplicon-specific KNEX-DNA-crystal. The amplicon-specific region of a functional oligonucleotide in the KNEX-DNA-crystal can hybridize with a target DNA molecule from a genomic DNA sample, which then primes a polymerization reaction. The original molecule will dissociate from the KNEX-DNA-crystal when denatured, but the newly synthesized fragment remains attached to the crystal. When the temperature is reduced, the newly synthesized fragment can hybridize with a neighboring oligonucleotide at the crystal. Target oligonucleotides that are attached to the KNEX-DNA-crystal have the highest probability for binding, which then in turn can start a polymerization reaction. This process can be repeated for several cycles. In this way, local specific amplification is achieved, with minimal interference of other oligonucleotides.

Figure 4A:
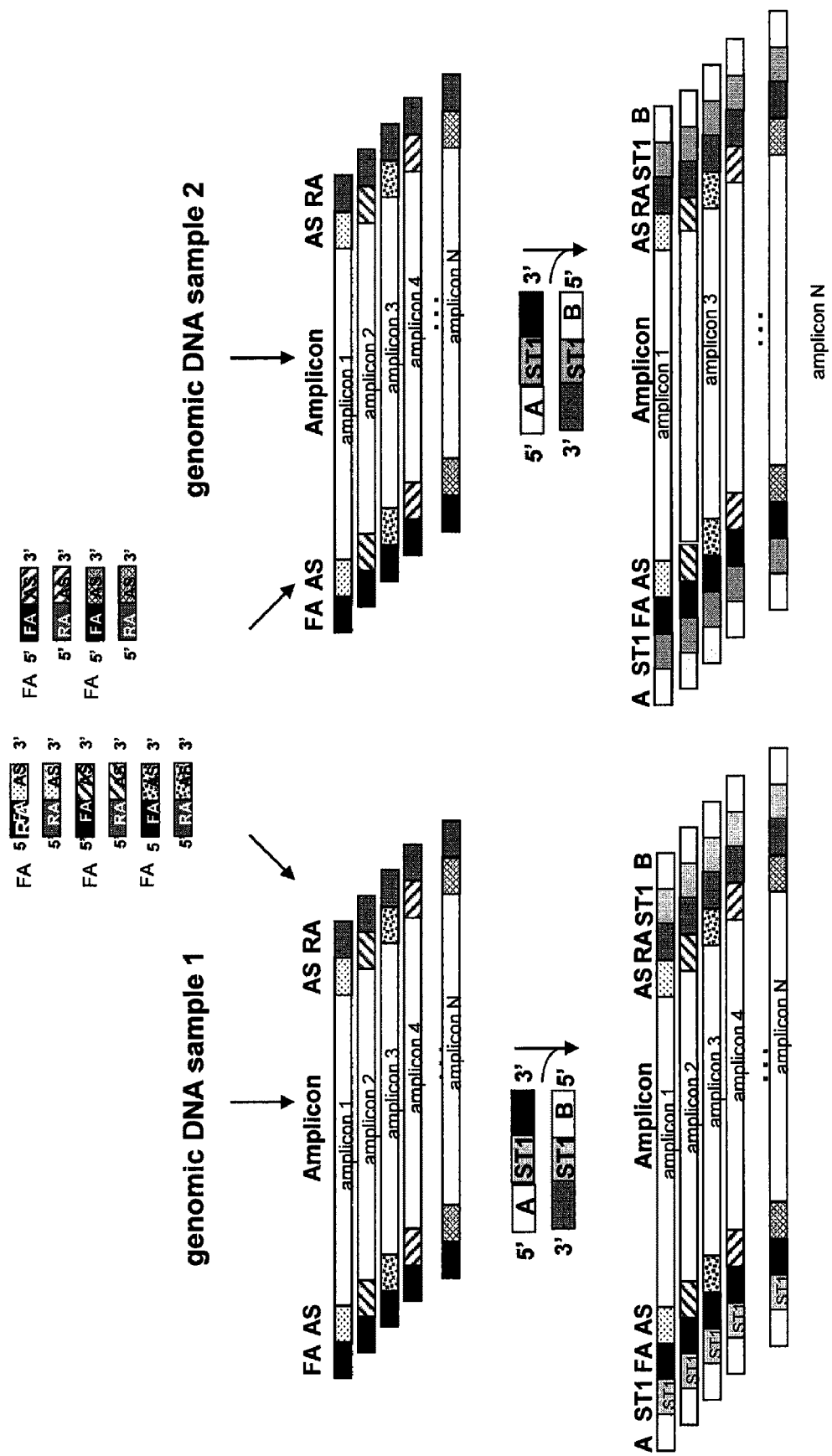
FIG. 4 shows an embodiment of the method of sample specific amplicon labeling.

FIG. 4a. Differently tagging of N amplicons from different samples using a 2-step PCR protocol, in which the tag is incorporated in the primers used for the second PCR step. Two samples are shown. N amplicons, for x samples, only (2N+2x) primers are needed. Of the latter, 2N primers are amplicon-specific primers (to be used for all samples), and 2x non-gene-specific primers (can be used for different genes).

Figure 4B:
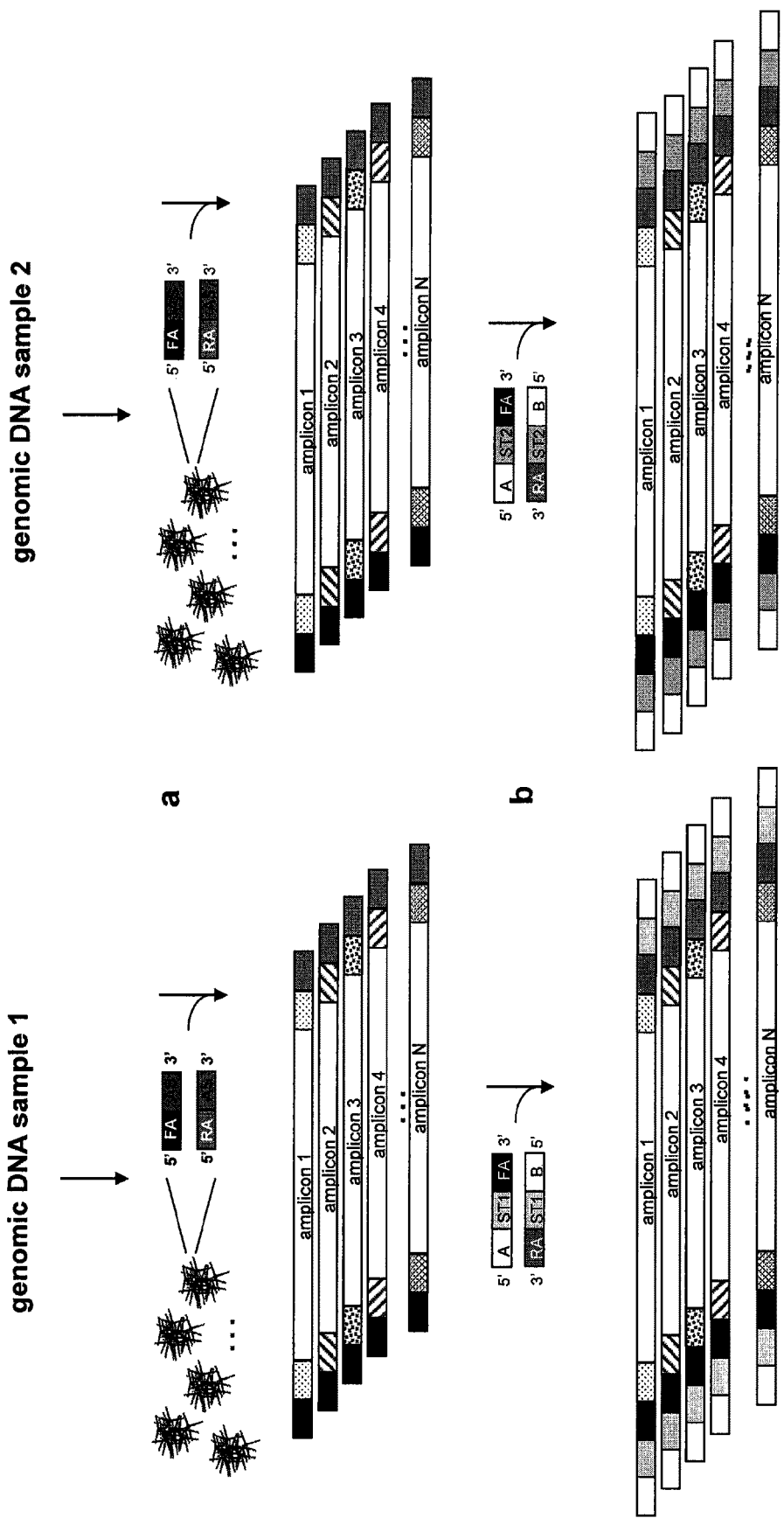

FIG. 4b. Use of amplicon-specific KNEX-DNA-crystals in multiplex amplifications and which can be specifically tagged by a sample tag.

The different primers used in each step of the process may have specific different melting temperatures, so that they can be specifically called in the process by their annealing temperature, and can therefore be mixed.

a. For each amplicon, KNEX-DNA-crystals were build with the 2 respective primers for amplification of that amplicon, and different amplicon-specific KNEX-DNA-crystals were combined in the reaction. Each forward primer contains an amplicon-specific region (AS) and a universal forward adaptor (FA), analogously the reverse primers contain an AS region and another universal reverse adaptor (RA). The KNEX-PCR reaction favors amplification of the specific, versus aspecific fragments. All PCR fragments will then carry identical sequences at their ends.

b. In a next amplification step, a sample tag (ST) is attached to each amplicon. By using a different primer pair per sample, all amplicons from one individual can be differently tagged from the amplicons from another individual. The forward and reverse primer may even contain a different sample tag (ST). This step also allows transfer of the amplicons (i.e. through the generation of their daughter amplicons) from a solid-phase status to a free status in solution, so that they can be easy manipulated in next steps. The primers are built up of three parts, the 3' end is complementary to the universal adapters attached in the previous step, allowing priming of all amplicons obtained in the previous step; a unique sample tag (ST), and a third adaptor (again different adaptors for the forward (A) and reverse primers (B)). The A and B adaptors will allow further manipulation, such as an water-in-oil-emulsion-PCR and pyrosequencing in a GS-FLX sequencing protocol.

Because of the use of sample-tagged fragments, all fragments from all individuals can now be processed simultaneously. After analysis, fragments can be traced to the original sample through the sample tag.

Figure 5A:
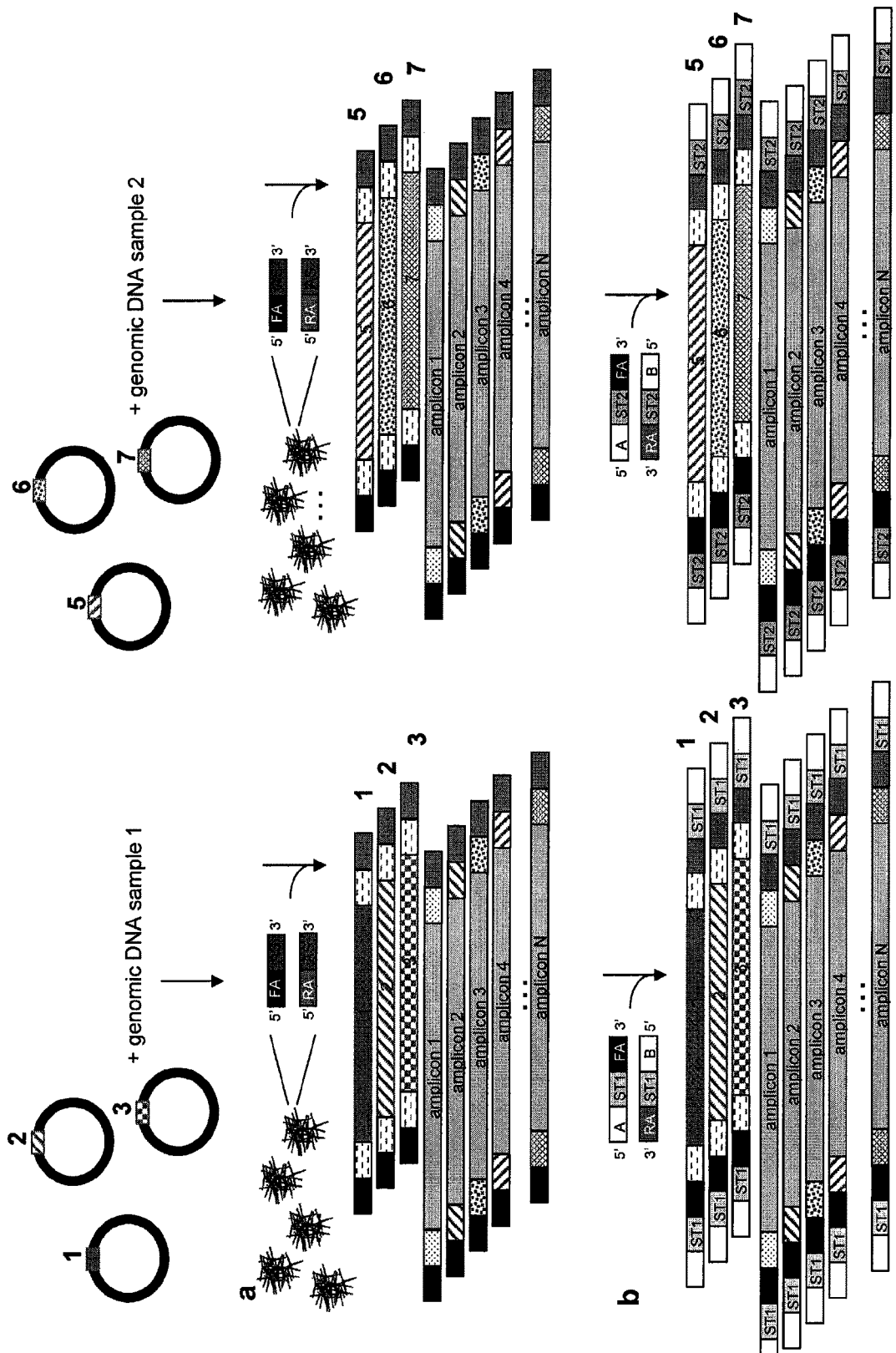

FIG. 5a shows the use of molecular bar code or marker nucleic acid molecules in multiplex parallel sequencing genetic tests.

The different primers used in each step of the process may have specific different melting temperatures, so that they can be specifically called in the process by their annealing temperature, and can therefore be mixed.

Three bar code molecules (also referred to as marker nucleic acids) are added to a sample to be analyzed, a different set for each sample. Then DNA is extracted, including the bar code molecules.

a. Then a KNEX-PCR reaction, enabling local efficient independent amplifications, is performed. For each amplicon, KNEX-amplicon-specific DNA-crystals are prepared containing the 2 respective primers for amplification of that amplicon, and different KNEX-DNA-crystals are combined in the reaction. Each forward primer contains an amplicon-specific region (AS) and a universal forward adaptor (FA), analogously the reverse primers contain an AS region and another universal reverse adaptor (RA). The KNEX-PCR reaction favors amplification of the specific, versus aspecific fragments. All PCR fragments will then carry identical sequences at their ends.

b. In this amplification step, a sample tag (ST) is attached to each amplicon. By using different primer pairs per sample, all amplicons from one individual can be differently tagged from the amplicons from another individual. The forward and reverse primer may even contain a different sample tag (ST). This step also allows transfer of the amplicons (i.e. through the generation of their daughter amplicons) from a solid-phase status to a free status in solution, so that they can be easy manipulated in next steps. The primers are build up of three parts, the 3' end is complementary to the universal adapters attached in the previous step, allowing priming of all amplicons obtained in the previous step; a unique sample tag (ST), and a third adaptor (again different adaptors for the forward (A) and reverse primers (B). The A and B adaptors will allow further manipulation, such as an water-in-oil-emulsion-PCR and pyrosequencing in a GS-FLX sequencing protocol.

Because of the use of sample-tagged fragments, all fragments from all individuals can now be processed simultaneously. After analysis, fragments can be traced to the original sample through the sample tag. Moreover, since the sample tag will be also attached to the fragments derived from the bar code molecules, it can be verified if one is still dealing with the original sample, so that no sample switching has occurred. The bar code molecules and sample tag will also allow automaton of laboratory and reporting protocols.

Figure 5B:
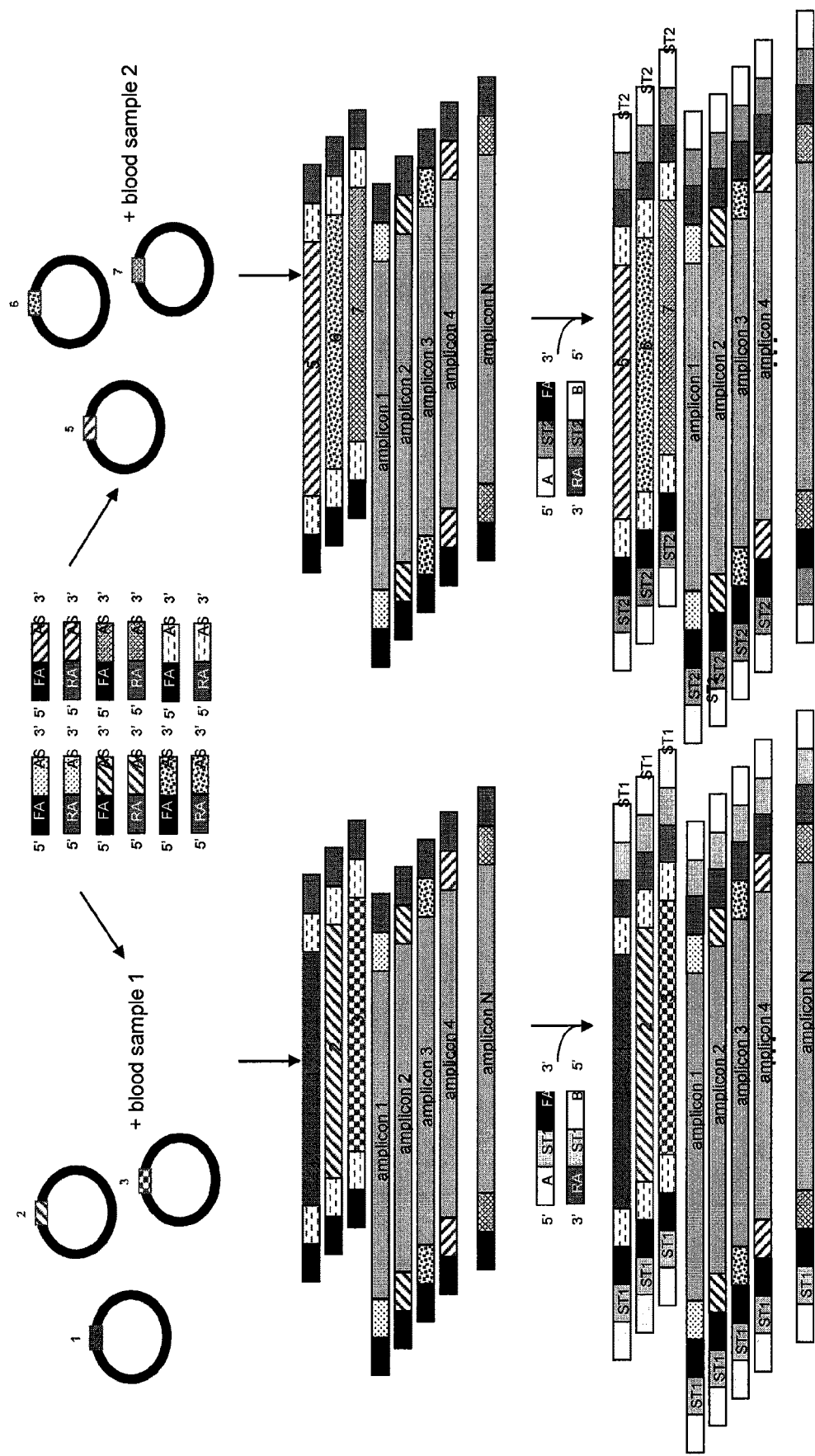

FIG. 5b. Same as FIG. 5a, but for any multiplex PCR amplification, rather than KNEX-PCR.

Figure 6:
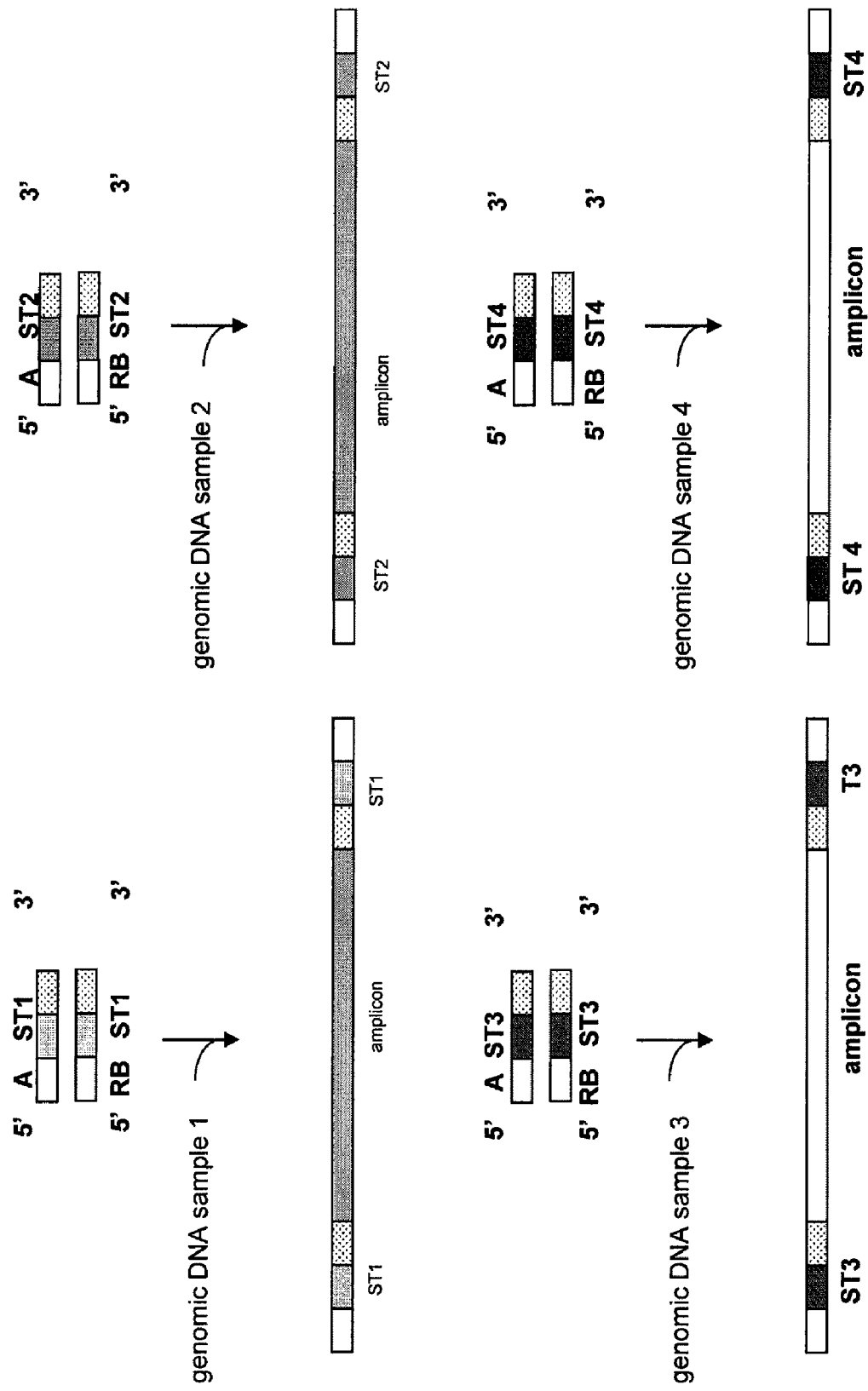

FIG. 6. Differently tagging of 1 amplicon from different samples using a 1-step PCR protocol, in which the tag is incorporated in the primers used for amplification. Four samples are shown. For x samples, 2*x different tagged primers are needed.

Figure 7:
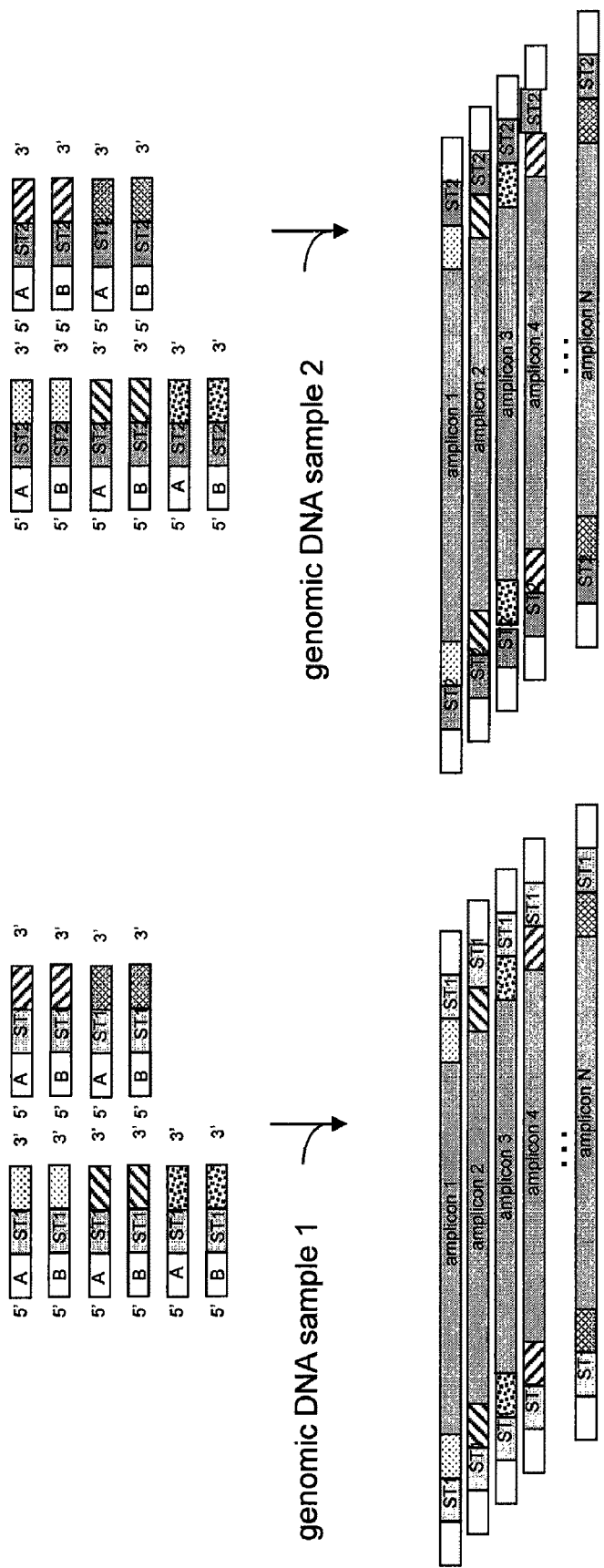

FIG. 7. Differently tagging of N amplicons from different samples using a 1-step PCR protocol, in which the tag is incorporated in the primers used for amplification. Two samples are shown. For N amplicons, for x samples, a total of 2*N*x different tagged primers are needed.

Figure 8:
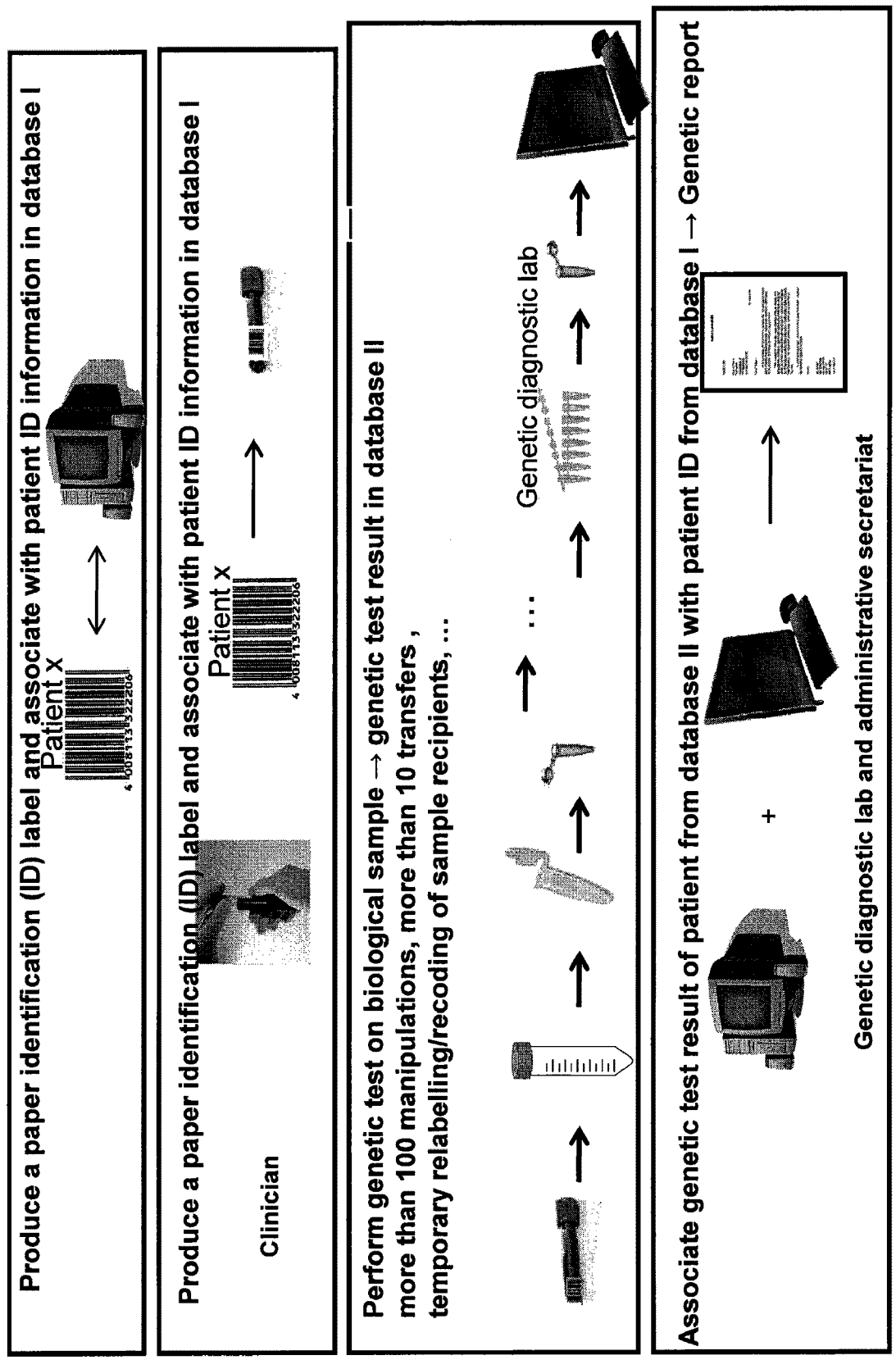

FIG. 8. Workflow of a sample for genetic testing, which involves many manipulations which are each prone to potential errors, such as sample switching, contamination, wrong association of patient name and test result in genetic test report, etc.

Figure 9:
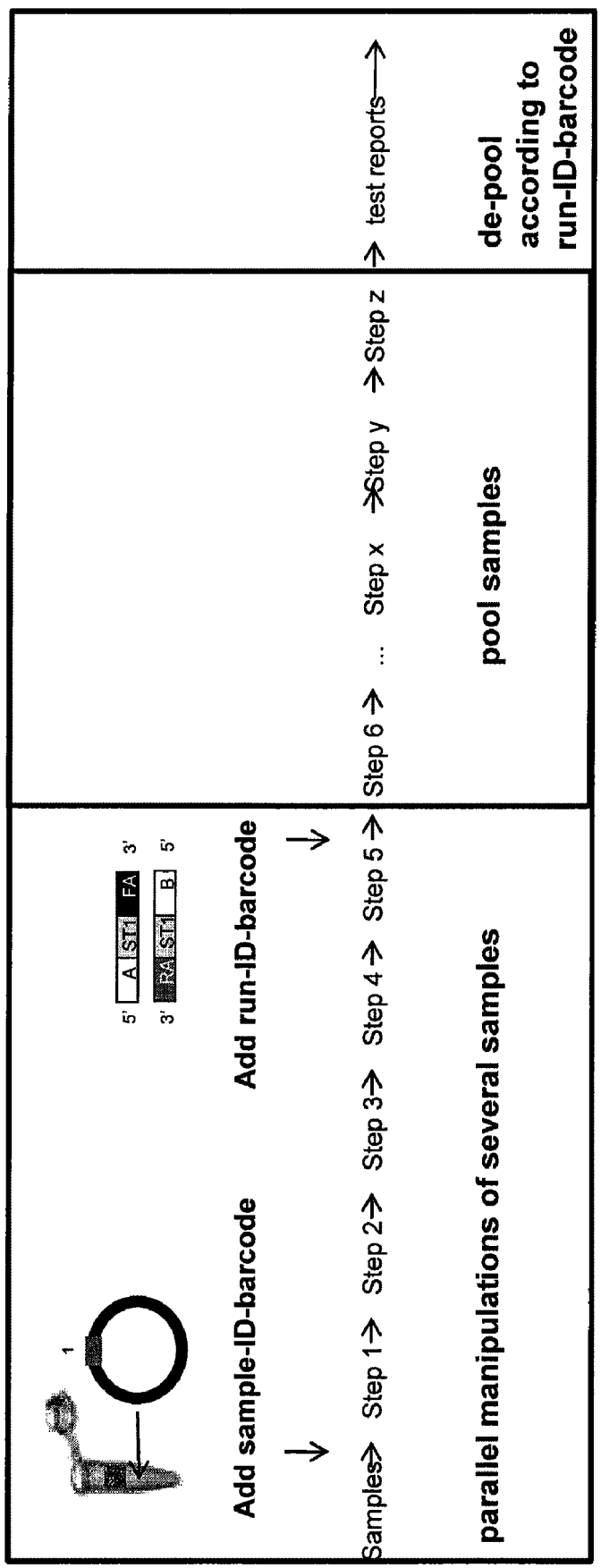

FIG. 9. Schematic workflow for genetic testing in a completely-quality assured process.
This is a schematic drawing of the workflow shown in FIG. 8. By means of a 2-step PCR protocol, a specific run-ID-barcode (molecular barcode—in the present invention to as sample DNA tag) can be introduced for each sample, after which all samples can be economically pooled and sequenced in parallel, and depooled after sequencing according to the respective run-ID-barcodes/sample DNA tags and analyzed. If another specific sample-ID-barcode is added upstream in the process (in the present invention also referred to as marker nucleic acids), and both the sample-ID-barcode (marker nucleic acids) and run-ID-barcode (sample tag) can be preferentially covalently linked, and analyzed in parallel with the amplicons under investigation, the test will be completely quality-assured from the moment when the sample-ID-barcode is added. The earlier the sample-ID-barcode is added in the protocol, the earlier the test protocol is quality-assured.

Figure 10:
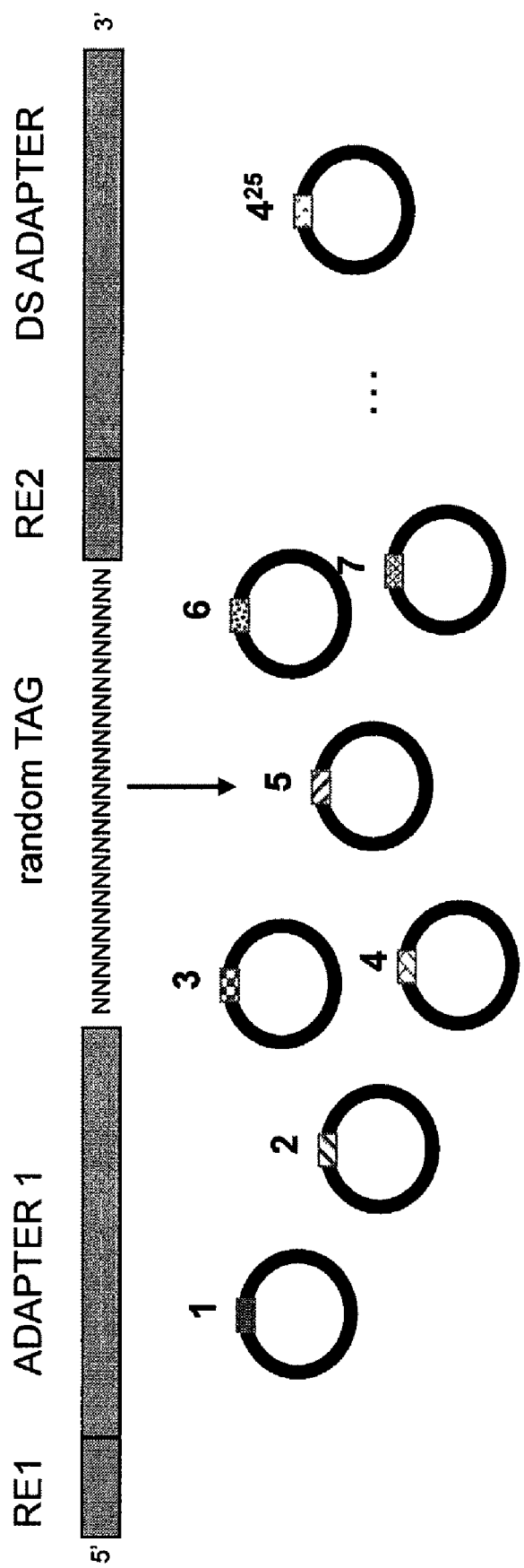

FIG. 10. Generation of libraries of molecular bar code molecules.
In a first instance a recombinant vector is generated that contains an adapter sequence. A first primer against this adapter sequence will allow amplification of the molecular bar code region in later steps. The adapter sequence is positioned so that PCR products of a reasonable length will be obtained in these later steps.
An oligonucleotide population, obtained in one oligosynthesis reaction, contains a 25-nucleotide long random tag sequence, flanked by two different restriction enzymes (RE). This will theoretically yield $4^{25}$ (1125899906842624) different oligonucleotides. They also contain a DS adapter sequence, which is used as a priming site in order to generate double stranded oligonucleotides. The random sequence contains also an adapter sequence, which will be used for binding of the second primer that will allow amplification of the molecular bar code region in later steps.
Cloning of these oligonucleotides will generate $4^{25}$ (1125899906842624) different types of bar code molecules. The format will allow generation of libraries without the need for immediate subcloning of all molecular bar codes. Subclones can be generated from this master library only when needed.

FIG. 11. Combining different 25 nt-random plasmids, rather than using a single 25 nt-random plasmid, allows the generation of an increasing number of sample-ID-barcodes (marker nucleic acids). Indeed, since the same run-ID-barcode (sample tag) will be added at the end of the protocol per sample, all but one of a given number of 25 nt-random plasmids in the sample-ID-barcode (marker nucleic acids) need to be different between samples in order to discriminate them. A limited number of 60 25-nt-random plasmids allows the generation of 1 million unique sample-ID-barcodes. This provides a means of using any sample-ID-barcode combination only once, excluding usage in more than 1 sample.
The run-ID-barcode will be added at the end of the sample processing at the individual sample level through a unique sequence tag (ST) present in primers used for amplification. Only a limited set of such primers is needed, which equals the numbers of samples analyzed in one sequencing experiment, which can be re-used in each new sequencing experiment.

FIG. 12. The correct barcode combinations should be found at the end of the process, i.e. the molecular bar code added at the start of the process (marker nucleic acid e.g. 1A) and the sample bar code added at the end of the process (sample tag e.g. 1B). Any deviation indicates an error during the process, such as sample switching, so that the test will not be valid. If more then the expected barcodes are found, a contamination can be concluded.

Figure 13:
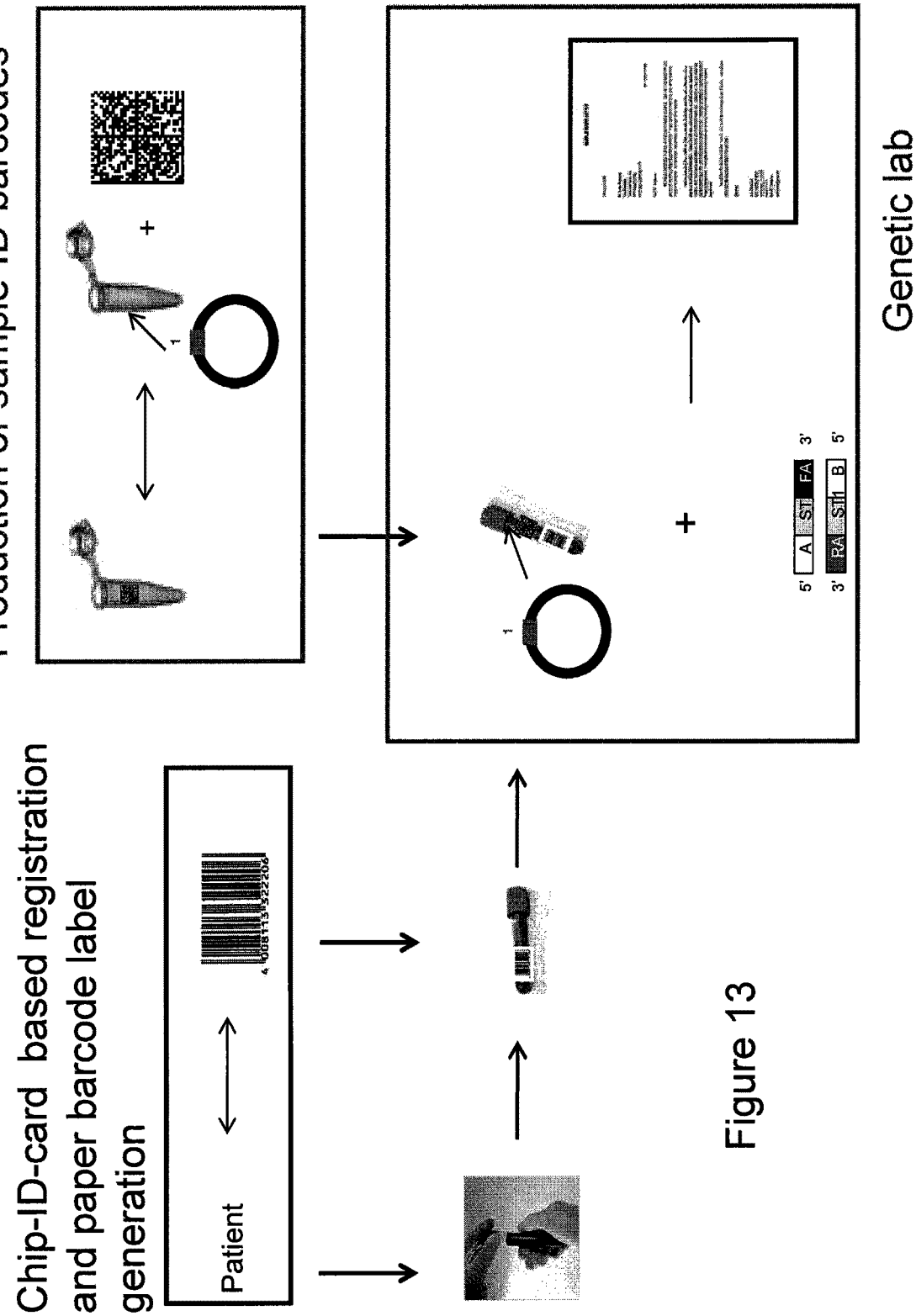

FIG. 13. The use of sample-ID-barcodes (marker nucleic acids) makes the complete genetic test quality-assured. Since that the production of sample-ID-barcodes can be performed in a robotic quality-assured process, as well as the registration and generation of barcode paper labels of the patient through the use of chip-ID-card identity based informatics systems, the only remaining potential errors are the isolation of the blood from the patient in a blood collector tube, attachment of the patient's barcode paper label to the tube, and addition of the molecular sample-ID-barcode (red arrows). The latter step can even be prevented if blood collector tubes would be produced in which sample-ID-barcode are already present.

Figure 14:
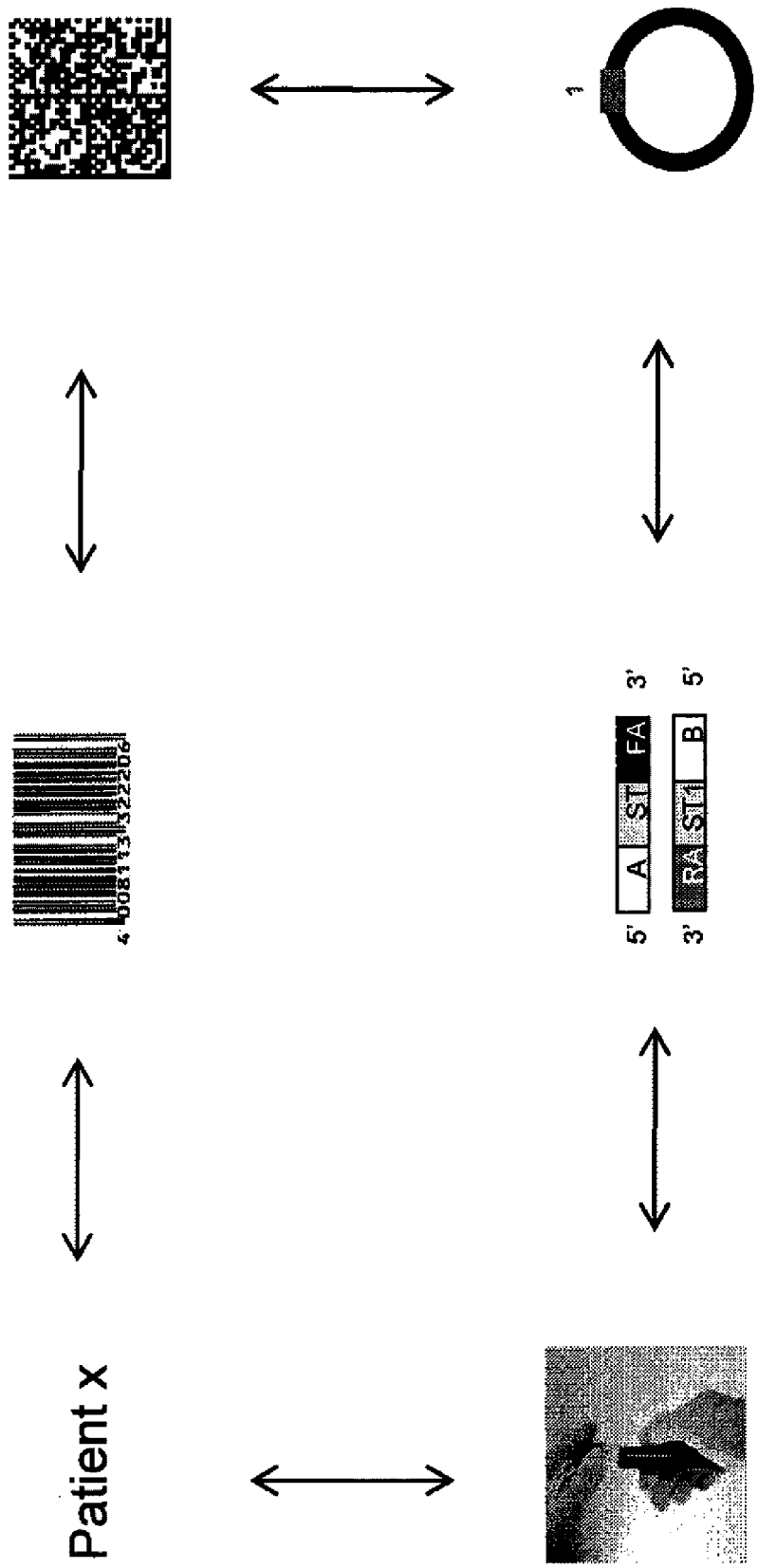

FIG. 14. The patient and all types of labels are linked. The molecular sample-ID-barcode-label is even read by the sequencer, besides the fragments under investigation. The sequencer can thus read the mutation and the name of the tested individual. This allows automation of the generation of a report in which patient name and genetic test result are combined from different databases without human intervention.

Figure 15:
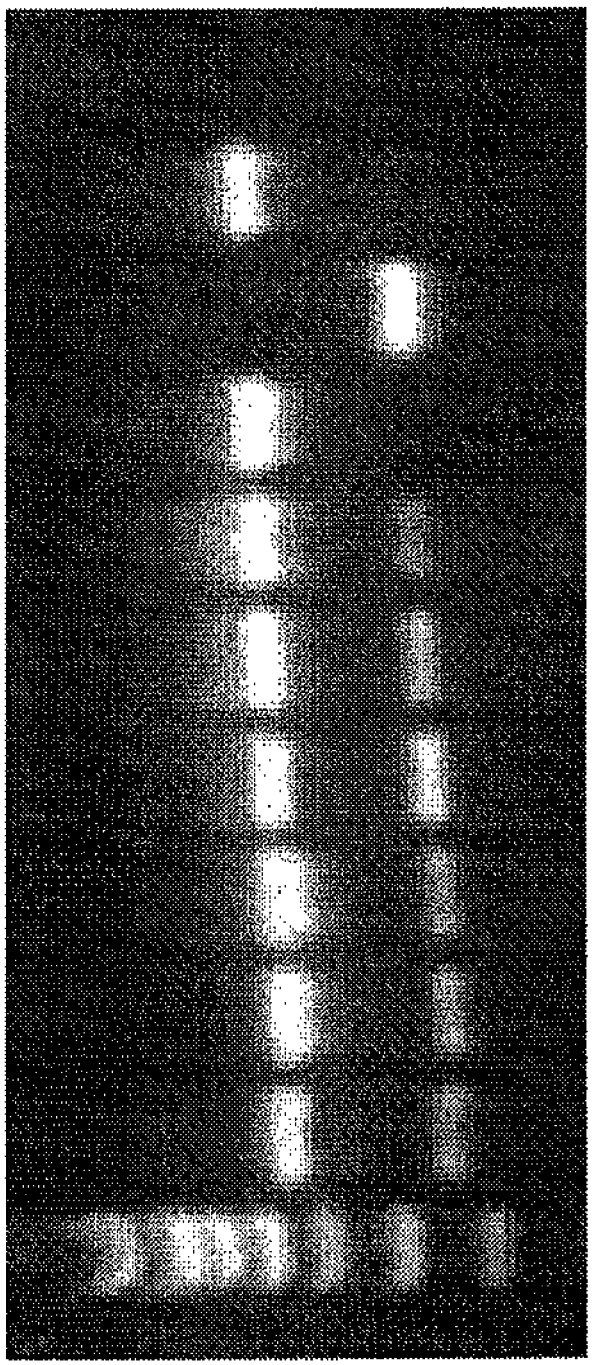

FIG. 15 visualizes by electrophoresis DNA fragments amplified using DNA KNEX crystals in a multiplex PCR.

DESCRIPTION

'core'-molecules and 'functional'-molecules: a 'core'-molecule in a KNEX-DNA-crystal in the context of the present invention is a molecule arm which essentially forms the frame of the KNEX-DNA-crystal, a 'functional'-molecule in a KNEX-DNA-crystal is a molecule which will be used in a particular process and that is attached to the frame of the KNEX-DNA-crystal. It is possible that a 'core'-molecule and 'functional'-molecule may be attached at a same junction. It is possible that the 'functional'-molecule has also 'core'-molecule properties, and vice versa.

"sample tag" also referred to as "DNA tag" or "run-ID-barcode" in the context of the present invention refers to known nucleic acid sequences which become covalently linked to DNA fragments and/or other nucleic acid molecules in the sample during amplification of the DNA fragments and/or other nucleic acid molecules in a 2-step amplification reaction.

"marker nucleic acids" or "molecular bar code molecules" or "sample-ID-barcode" in the context of the present invention refers to known nucleic acid sequences which are added to the sample to be analyzed as soon as possible, and which are subject to the same processes (simultaneously, in the same mixture or in parallel) as the DNA fragments, present in the sample to be analyzed.

Robust multiplex PCR reactions of a large number of amplicons may be achieved when the different primers are physically restricted. Here we propose different methods to trap molecular components allowing a physically restricted amplification with minimal interference of other molecular components.

In a first method, for each DNA fragment that one wants to analyze, two primers that bind to this fragment and that allow amplification of that DNA fragment, are bound to beads, e.g. two biotinylated primers bound to streptavidin coated beads. In an analogous manner, beads are made for each DNA fragment that one wants to amplify, using specific primers to the respective DNA fragment. In the final multiplex amplification reaction, an aliquot of all these different beads mixtures is pooled. Although free primers may be still in solution, specific amplification will mainly occur at the beads, and primers bound to a bead will have the highest probability of priming the specific PCR reactions at that bead, therefore allowing physical restriction of different amplification processes, thereby increasing the efficiency of the multiplex amplification. However, because of their gravity, beads will sediment to the bottom of the solution, thereby hampering the amplification. This can be overcome by restricting the beads themselves, e.g. by binding them to the wall of tubes, e.g. streptavidin-coated PCR tubes.

Another means would be the construction of light molecular structures, instead of beads, to which the primers are bound and which therefore remain in solution. Again here, they may be in turn fixed, e.g. to the wall of tubes. Such molecular structures might be obtained, as, what we call, molecular KNEX-DNA or molecular KNEX-DNA-crystals (see FIG. 1). In KNEX-DNA structures, the two types of amplicon-specific primers are bound many times at different positions to another DNA molecule, and/or a network of smaller DNA molecules (e.g. oligonucleotides). KNEX-DNA crystals were chosen because small DNA molecules, and modifications thereof, are easily synthesized, modified and manipulated using well established technology at an economical price. This even applies to larger DNA molecules, such as plasmids. Indeed, by techniques such as nick translation, modified nucleotides can be incorporated allowing the formation of KNEX-DNA. The term DNA molecule includes linear oligomers/polymers of natural or modified monomers or linkages, e.g., deoxyribonucleosides, ribonucleosides, anomeric forms thereof, peptide nucleic acids (PNAs), and the like, the monomers are linked by phosphodiester bonds, or analogs thereof. The DNA molecules of the present invention can include non-natural nucleotide analogs. For the preparation of amplicon-specific crystals, other polymer forming molecules may be eventually used.

A KNEX-DNA-crystal used for PCR amplification of a given amplicon is called an amplicon-specific KNEX-DNA-crystal. In an amplicon-specific KNEX-DNA-crystal, the 2 amplicon-specific primers for amplification of a given amplicon in a PCR reaction are physically restricted and in close proximity, so that amplicons are amplified in/at their own crystal containing its own 2 amplicon-specific primers, with no, or minimal, interference of other primers in the solution. Therefore, isolated PCR reactors will be generated containing the 2 amplicon-specific primers in a tube, so that different amplicon-specific KNEX-DNA-crystals, which were prepared separately in a bulk solution, can be combined in a single multiplex PCR reaction.

These amplicon-specific primers may potentially contain an adaptor sequence, which is shared by all, or part of all, amplicon-specific primers, for cleavage and/or binding to universal primers in potential later steps of a process. A cleavable site might also be introduced by other means, such as a site in the oligonucleotide that can be cleaved by photons (UV-light). Another cleavable linker could be a disulfide, in which the cleavage occurs by a reducing agent, for example dithiothreitol (DTT), beta-mercaptoethanol, etc.

Since that each amplicon is amplified isolated at its own crystal-reactor, once that the amplification conditions for an individual amplicon have been optimized, there will be no, or minimal, need for empirical multiplex PCR optimization and design. Moreover, the number of amplicons that can be multiplexed may exceed 10-100 amplicons, so that this step can be easily transferred to any other gene, and even large or multiple genes.

The cross linking of the components in the KNEX-DNA-crystal may be achieved by any manner known in the art. It can be either a covalent or non-covalent interaction. Covalent chemical crosslinking can be accomplished using standard coupling agents. For example, water-soluble carbodiimide can be used to link the 5'-phosphate of a DNA sequence to an amine-moiety through a phosphoamidate bond. Other linkage chemistries to join an oligonucleotide include the use of N-hydroxysuccinamide (NHS) and its derivatives, for example.

Other examples of interactions which can form the basis for crosslinking include interactions between biotin/streptavidin, biotin/avidin, biotin/biotin-binding-molecule (e.g. NEUTRAVIDINT modified avidin (Pierce Chemicals Rockford, Ill.), glutathione S-transferase (GST)/glutathione, antibody/antigen, antibody/antibody-binding-molecule, dioxigenin/anti-dioxigenin, DNP(2,4-dinitrophenyl)/anti-DNP antibodies, maltose-binding-protein/maltose, chelation (e.g. ($Co^{2+}$, $Ni^{2+}$)/hexahistidine, pluronic coupling technologies, and so on.

A crystal might be even formed without the use of true separate junctional molecules, such as the use of oligonucleotides containing psoralen moieties, or even by Watson-Crick base pairing between oligonucleotides themselves. The latter may nevertheless even contain binding moieties, e.g. biotin, not for the purpose of forming the crystal but for adding functional groups to the crystal needed for later processing of a crystal. Depending of the type of crosslinking, some structures will be more stable and therefore more useful in certain applications. E.g. complexes that are made through Watson-Crick base pairing between oligonucleotides, and that are used for amplification, may decompose during a denaturation step at 94° C.

Figure 1:
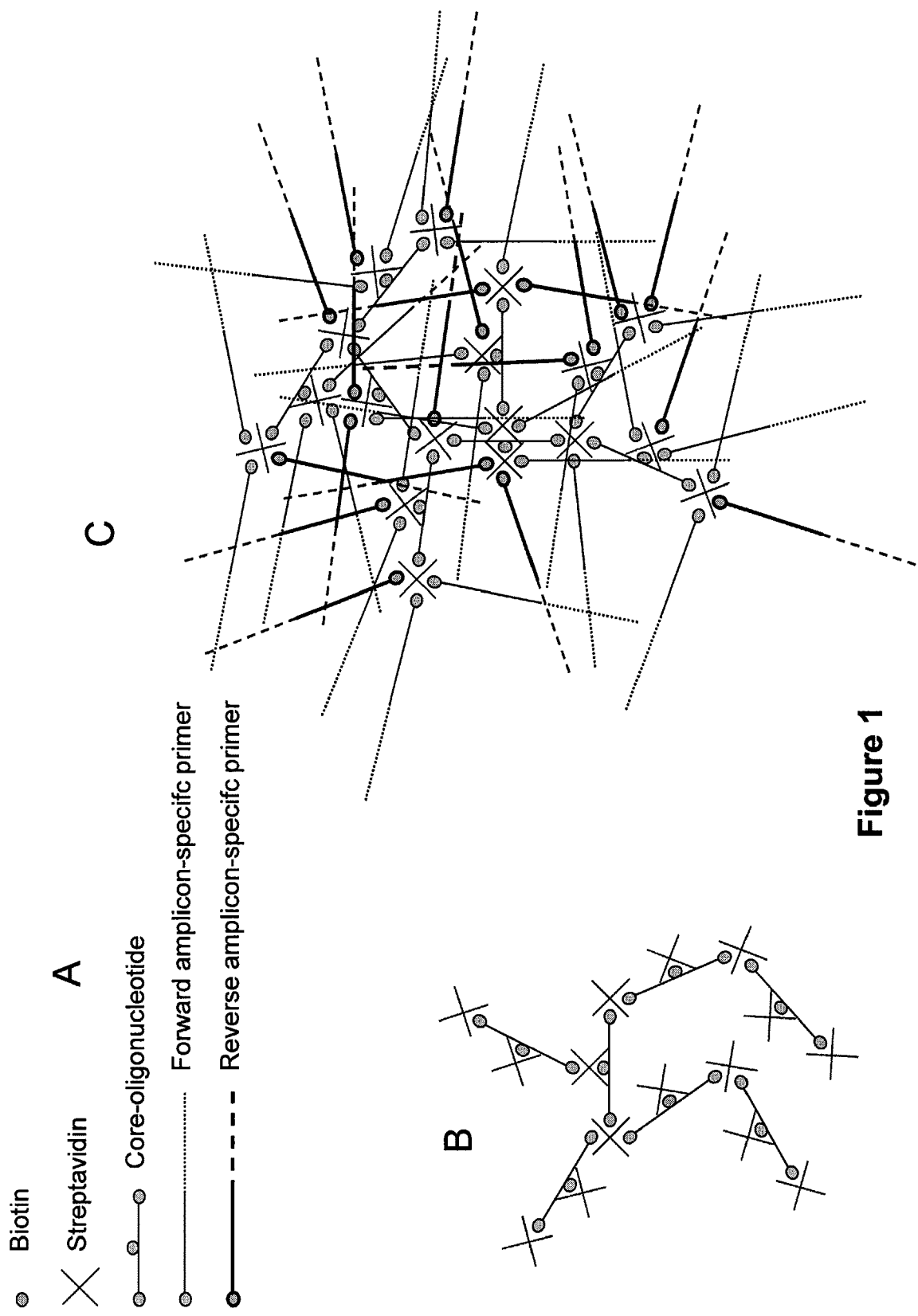
Figure 2:
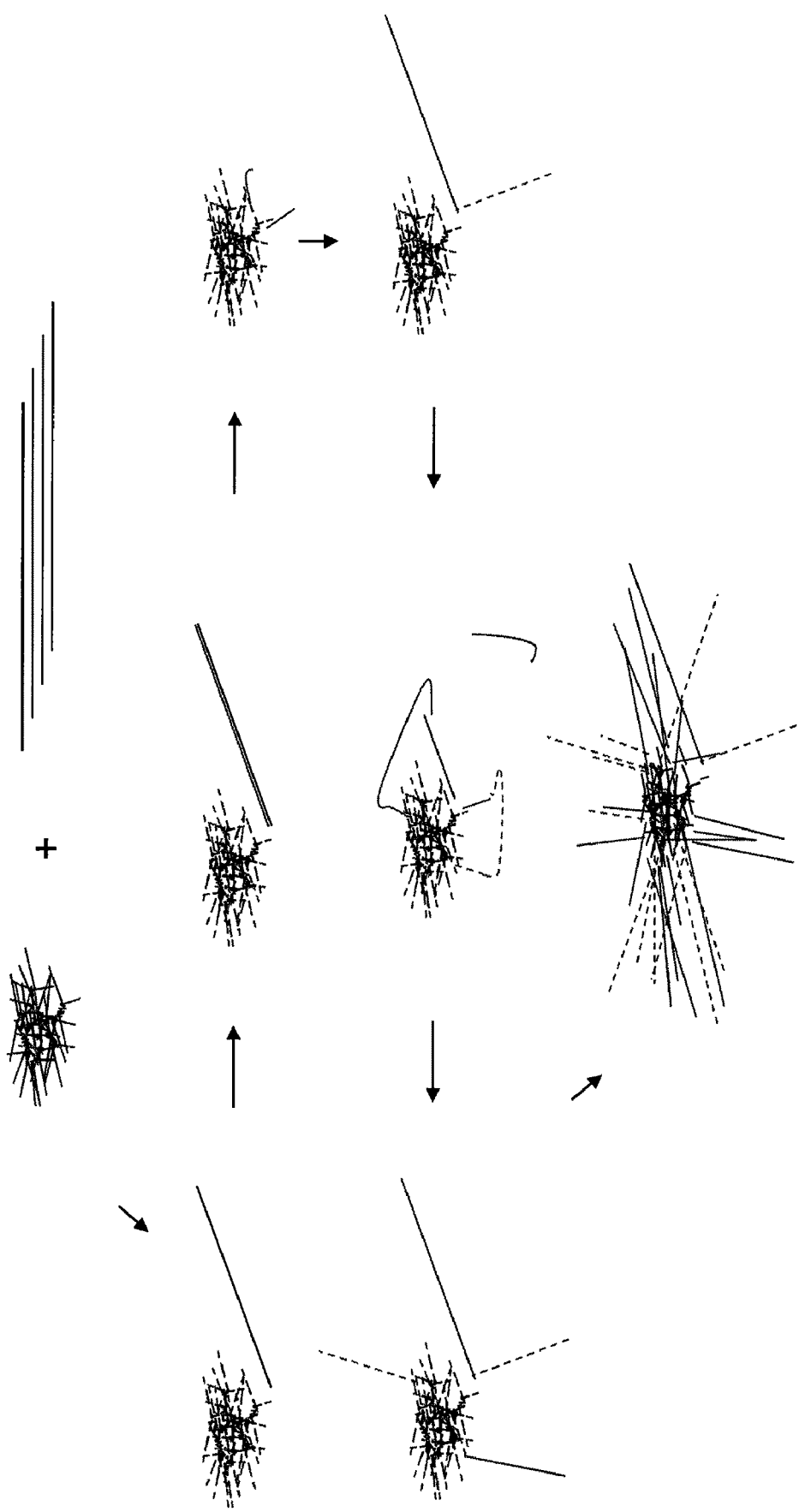

Specifically we describe here KNEX-DNA-crystals where the crosslinking is realized by biotin and streptavidin (FIGS. 1 and 2).

The DNA-core molecule of a KNEX-DNA-crystal can be 1 'core'-oligonucleotide that carries at least two biotin groups, at its 5' end, its 3' end, and/or internal sites. To a solution containing 'core'-oligonucleotide, streptavidin is added, as well as the two amplicon-specific primers are added. Sub-solutions may first be prepared of some of these components, but a some stage they end up complexing in the same solution. Indeed, the order and amount by which the different components are added might affect the composition. Certain compositions may be better suited for certain amplifications. For example, addition of the 'core'-oligonucleotide and streptavidin may form molecular type of beads, and subsequent addition of the amplicon specific primers may cover the surface of the molecular beads. Each streptavidin molecule is able to bind four biotin groups, and therefore a three-dimensional network or KNEX-DNA-crystal is formed between the three oligonucleotides. The density of each type of oligonucleotide in the KNEX-DNA-crystals can be controlled by the ratio of 'core'-oligonucleotide to the 2 amplicon-specific primers, as well as by the concentration of streptavidin. Even the ratio of the 2 amplicon-specific primers may be controlled. After crystallization, free biotin might be added to saturate the still free binding sites on streptavidin molecules, so that different amplicon-specific KNEX-DNA-crystals will not aggregate when mixed. If certain amplicons remain difficult to be amplified in the multiplex PCR, different KNEX-DNA-crystals may be evaluated. For example, KNEX-DNA-crystals in which the 'core'-oligonucleotide contains varying numbers of internal biotin groups, so that the local concentration of particular amplicon-specific primers is further increased. By keeping incubation times during an amplification step limited, diffusion of products may be even more restricted. Possibly one or both primers should be still freely available to some extent in the PCR reaction in order to obtain the most efficient amplification process. Example 1 shows a proof of principle experiment.

Rather than an oligonucleotide, larger DNA molecules can be used as core-DNA molecules in KNEX-DNA crystals. For example, plasmid DNA, either linearized or not, can be biotinylated by nick translation to varying extents depending on the relative concentration of biotinylated nucleotide building blocks.

Each core of the KNEX-DNA-crystal might be 1 DNA molecule, such as an oligonucleotide with at least 2 biotin groups; or an aggregate of different DNA molecules, such as oligonucleotides with at least 2 biotin group that are polymerized, linked by streptavidin molecules or base-pairing. Each of these latter DNA molecules preferentially contains at least two different biotin groups and different types of such oligonucleotides might be used (i.e. oligonucleotides having different sequence and/or modifications). This is a more economical and easier way to synthesize large core-molecules, and allows the synthesis of a KNEX-DNA-crystal were amplicon-specific primers are more physically spread over the crystal.

The preparation of such structures may not be 100% efficient, so that all components are not incorporated in the KNEX-DNA-crystals and may be present as individual components in a solution. It is also possible that during later processing of the crystals, part of the crystals will degrade partly or complete, possibly only temporally, to their individual components of which the crystals were built up. During processing of a solution containing these crystals, as well as the free components, these free components may interfere in later processing. Their contribution may improve or worsen the actual processing of the crystal, or have no effect at all.

Figure 3:
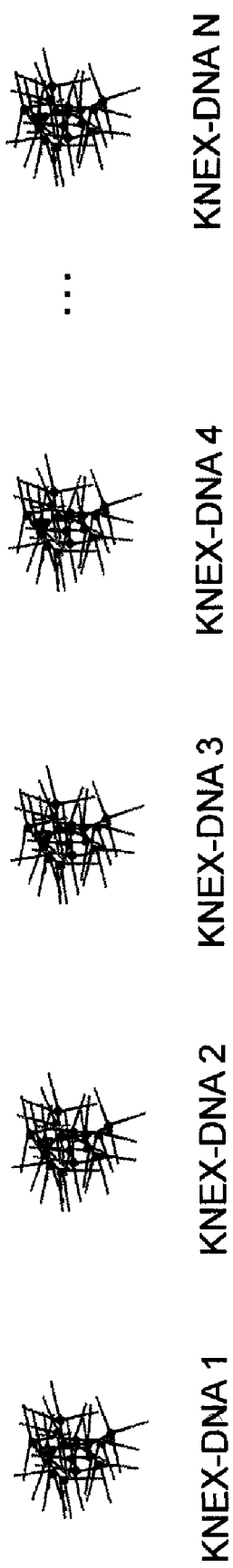
FIG. 3 shows different amplicon-specific KNEX-DNA-crystals, each containing two different functional oligonucleotides that allow amplification of one specific amplicon and are prepared separately. Different amplicon-specific KNEX-DNA crystals can be pooled in one mixture so that the different types of amplicons are generated in an isolated means in the mixture.

In a multiplex PCR amplification of amplicon-specific KNEX-DNA-crystals, different amplicon-specific KNEX-DNA-crystals will be mixed. For each amplicon-specific KNEX-DNA-crystal, two amplicon-specific primers will be used, so that all these different amplicon-specific KNEX-DNA-crystals have to be synthesized separately, and should be mixed afterwards (FIG. 3). This should be, once optimized, be done only once, and therefore in bulk and with minimal effort.

The presence of a biotin at the 3' end of the core-DNA molecule (e.g. oligonucleotide) will not allow priming or interference in a PCR reaction. The sequence in this 'core'-oligonucleotide can be also used for specific functions, such as binding to other oligonucleotides (e.g. for capturing). Also it may contain recognition sites for restriction enzymes, so that after binding to a complementary oligonucleotide, the KNEX-DNA-crystal can be cleaved after the amplification step (e.g. for disruption of the KNEX-DNA-crystal, so that amplified material becomes more accessible in later steps of a protocol). The latter might be also achieved by a cleavable linker (e.g. by UV) in the 'core'-oligonucleotide, which would be a more universal means of cleavage than the use of restriction enzymes, since a particular recognition site for a restriction enzyme might be present in the amplified amplicon.

In KNEX-DNA-crystals, the 2 amplicon-specific primers are possibly positioned in a 3-dimensional structure. This may affect the efficiency of amplification. When the 2 amplicon-specific primers are bound to beads they are only positioned on a 2 dimensional surface. Since KNEX-DNA-crystals have a relatively low molecular weight, they remain homogenously solubilized in the reaction mixture and are readily accessible to reagents.

By reducing the specific incubation times and/or temperatures to a strict minimum, one will limit the extent of diffusion of products that are generated in a process, and in this way promote local processing of products.

KNEX-DNA-crystals may be even build up by 2 to 4, or even more, biotinylated 'core'-oligonucleotides in a more programmed manner. The formation of the crystals, i.e. the binding of the 'core'-oligonucleotides through biotin-streptavidin bounds, may be preceded by self-mediated DNA assembly of these 'core'-oligonucleotides. This self-mediated DNA assembly may allow the formation of rather specifically well-designed KNEX-DNA-crystals.

One could overcome the preparation of amplicon-specific structures (amplicon-specific beads, amplicon-specific KNEX-DNA crystals) if adaptors are added to the amplicon specific primers. In that case, only one type of KNEX-DNA structures containing only the two primers directed to the adaptor sequences needed to be prepared. Preferentially, the forward amplicon-specific primers contain a specific type of adaptor, while the reverse amplicon-specific primers contain another specific type of adaptor.

Alternatively, a standard multiplex amplification might be developed in a more robust way using solely amplicon specific primers that also contain an adaptor, preferentially a different adaptor for the forward primer than the reverse primers. However, all forward amplicon-specific primers carry the same adaptor, while all reverse amplicon-specific primer carry the same other adaptor. First, all amplicon-specific primers (with their adaptors) are added together and a classical PCR reaction is performed for a few cycles. In classical multiplex PCR reactions, the aspecific amplifications and the inefficient amplification of specific fragments increases with the number of cycles. If only a few cycles are performed, the specific fragments are still present in a relative high proportion, and if they proceed in a second more specific PCR step, with only 2 primers directed against the adaptor sequences of the first primers, they are more favorably amplified. Moreover, since all fragments then have a common priming site, there will be less primer-dependent preferential amplification that is observed in a classical multiplex PCR reaction. Moreover, if amplicons are designed in such a way that they have a similar length, there will be also no amplicon-length dependent specific amplification. One could also further enrich the specific amplification fragments from the aspecific fragments, through binding of the PCR products obtained after the first or second round of PCR to a molecule, or molecules, that recognize the desired fragments.

One could also perform an enrichment of the target DNA to be sequenced before the amplification step, which would reduce aspecific binding of primers during PCR. For example, in case that one wants to amplify the different exons of a given gene, one could hybridize total genomic DNA, either fragmented or not (e.g. by a (rare-cutter) restriction enzyme) to (a) DNA fragment(s) that contain sequences of this gene itself. For example, this could be a plasmid containing a cDNA derived from a transcript from this gene. In that case, they will bind all homologous genomic DNA fragments at the respective site of the coding sequences. This DNA fragment used for capturing cannot be a template in the subsequent PCR reaction, since all primers are located to intronic regions. The plasmid itself could be biotinylated by nick translation, which than can be bound to streptavidin-coated tubes, or streptavidin-coated beads (e.g. streptavidin-coated magnetic beads), and in this way would be an easy means in further separation steps.

At this moment, most genetic tests only analyze the coding region of a gene, i.e. the exons and their exon/intron junctions. Such tests will benefit from robust multiplex amplifications. However, in instances were also complete introns need to be analyzed, covering the whole gene in amplicons in a multiplex PCR reactions may be still too challenging, given the size that some genes can obtain. Here, a strategy could be to enrich the complete gene through hybridization of total DNA (genomic DNA, mitochondrial DNA, ... ), either fragmented or not (e.g. by a (rare-cutter) restriction enzyme) to (a) DNA fragment(s) that contain sequences of this gene itself. For example, this could be again a plasmid containing a cDNA derived from a transcript from this gene. These plasmids will then bind all targeted DNA fragments from a genomic sample at exonic regions. If the DNA was cut with a rare-cutter restriction enzyme, also intronic sequences will be captured together with the exon sequences. The plasmid itself could be biotinylated by nick translation, which than can be bound to streptavidin-coated tubes, or streptavidin-coated beads (e.g. streptavidin-coated magnetic beads), and in this way would be an easy means for isolation of the relevant fragments. The isolated fragments could then be amplified by PCR using random primers. Preferentially the random primers contain adaptor sequences for further processing in sequencing protocols, either after size-fractionation or not. On the other hand, the enriched DNA fragments can feed in standard sequencing protocols, such as the generation of a DNA-library. This enrichment step could be also performed after the generation of a DNA-library in a standard sequencing protocol, rather then before the generation of the DNA library. The latter protocol would have the added advantage that only sequences of the DNA sample under investigation will be sequenced, and not the plasmid that was used for isolating/enriching the target DNA. Indeed, these plasmids could in the end possibly 'contaminate' the sample under investigation. Since the adaptor sequences that are added to the different DNA molecules of a DNA library only allow further processing in the sequencing protocol, plasmids used for enrichment will not contain these adaptor sequences so that they cannot be processed or sequenced further.

This strategy could be even applied for more than 1 gene, i.e. different plasmids directed two the different genes under investigation that are combined (e.g. all genes involved in a given pathway or disease, all genes belonging to a certain class of proteins). Analogously, one could even enrich complete genomic regions, e.g. through the use of BAC-clones that recognize the region to be sequenced and therefore provide a means for enrichment of a subgenomic region.

An analogous strategy could be also used for enrichment of RNA (either converted to cDNA or not), than DNA.

New techniques allow the generation of large amounts of data, e.g. sequence data. They may even generate much more sequence than needed for the analysis of one sample. In order to make full use of the capacity of a technique, and therefore at an economical cost, different samples need to be mixed in one single experiment, in which each sample is tagged differently. The characterization of the tag in the final analysis allows the identification of the sample of which the fragment was derived, while the characterization of the attached fragment will allow analysis of the fragment under investigation of that sample.

Addition of a DNA-tag to a DNA fragment of a sample that one wants to analyze can be obtained in an amplification process in which at least one amplicon-specific primer contains the tag as an adaptor. However, this will be still very costly (FIG. 6 for one amplicon, FIG. 7 for several amplicons). E.g. when one wants to analyze 30 amplicons (60 primers) in one sample, and one wants to combine 200 samples, one needs 12000 primers if a tag is included in both amplicon-specific primers, and 6030 primers if a tag is included in one of the two amplicon-specific primers.

A much lower number of primers will be needed if tagging is performed in a two step protocol using adaptors, which is illustrated here (FIGS. 4*a* and 4*b*). In the first PCR reaction, amplicon-specific primers with an adaptor are used. All forward amplicon-specific primers contain the same adaptor, all reverse amplicon-specific primers contain the same other adaptor. In a second PCR reaction, primers are used directed against these adaptor sequences. They all include a unique tag sequence, and possibly additional adaptor sequences for further processing. In such a strategy, only 460 primers are needed if two tags per amplicon are included, or 260 primers if only one tag is included.

Moreover, the adaptor tag primers can be used for any amplicon, irrespective of the genomic region, or gene, from which it was derived, if all first step PCR reactions are performed with adaptor-amplicon specific primers that contain the same 'universal' forward and reverse adaptors.

Therefore, it is another object of the present invention to provide a method for introducing a DNA tag into a DNA fragment (FIG. 4*a*), including cDNA fragments, derived from a sample comprising genetic material the method comprising the steps of: (i) the amplification of a first DNA fragment in a first PCR-reaction using a first set of amplicon specific primers, each of the primers comprising an adaptor, preferably one adaptor for the forward primer and another adaptor for the reverse primer, and (ii) subsequently amplifying the first DNA fragment in a second PCR reaction using a second set of primers directed against the adaptor sequences, wherein either or both of the second set of primers comprises a DNA-tag.

In a more preferred embodiment, a same tag is introduced in more than one DNA fragment derived from a sample, the method comprising the steps of (i) the amplification of a first set of DNA fragments in a multiplex PCR-reaction or multiple PCR reactions running in parallel (in the context of the invention considered to be multiplex-like PCR e.g. emulsion PCR technology, or Fluidigm's Integrated Fluidic Circuits technology) using a first set of amplicon specific primers, wherein each forward primer of the set of amplicon specific primers comprises a same adaptor and wherein each reverse primer of the set of amplicon specific primers comprises a same adaptor and (ii) subsequently amplifying the first set of DNA fragments in a second PCR reaction using a second set of primers directed against the adaptor sequences, wherein either or both of the second set of primers comprises a DNA-tag.

Advantageously, either or both of the second set of primers comprise one or more additional different adaptors for further processing purposes.

Through careful design of the oligonucleotides, and/or concentrations of primers used, one could mix all primers in one reaction, so that only certain primers participate in a process at a given moment. E.g. in a two-step PCR assay, in which the oligonucleotides that are used for priming in the first amplification step have a higher melting temperature than the oligonucleotides that are needed in the second PCR process, one could add all primers together in one tube; if the PCR profile is first programmed for the first cycles to use an annealing temperature that uses a melting temperature of the first set of oligonucleotides, only these oligonucleotides can act preferentially as primer; if in later cycles the annealing temperature is lowered, the other primers are able to prime the amplification. Of course, the first primer pairs are still able to prime reactions, however if they were initially added at a much lower concentration, the second set of oligonucleotides will be kinetically favored.

The introduced DNA tag is a known nucleic acid sequence, more preferably the DNA tag comprises one or more primary tags wherein each primary tag comprises a known sequence. The DNA tag may comprise a repetition of a same primary tag. For example, tags composed of 5 nucleotides will allow 1024 unique different tags. It should be noted that nucleotide incorporation errors can be introduced in an oligosynthesis reaction. Especially in assays in which single molecules are analyzed, such synthesis errors may not be tolerated. Indeed, a synthesis error will change the identity of the tag, and the attached fragment will be incorrectly correlated with the wrong sample. This may be overcome by repeating the tag one or several times in the tag-oligonucleotide. For example, in tag-oligonucleotides in which the 5-nucleotide tag is repeated 4 times. it will be unlikely that the same synthesis/processing error occurs in each of the 4 tags. Identification of the sample will then be done on the basis of the tag that is most observed in a 4 5-tag sequence (e.g. 3 out of 4 tags are identical, while the fourth tag has one nucleotide difference). The repetition of a tag will provide a means to detect, and possibly correct, the misincorporation errors of oligonucleotides through synthesis. This repetition strategy might me combined by other strategies aiming to correct for incorporations, such as error-correcting barcodes (1).

The origin of each amplicon, i.e. the DNA of the individual from which the PCR fragment was generated, can thus be determined through characterization of the tag region, either found at the 5'-end and/or 3'-end, e.g. by sequencing. The remainder sequence of the amplicon will allow the analysis of the sample.

Thus, the present invention provides a method for introducing a DNA tag into one or more DNA fragments derived from a sample and verifying the origin of the one or more DNA fragments through the sequencing thereof wherein the method comprises the steps of:
  (i) introducing a DNA tag into the one or more DNA fragments comprising (a) the amplification of the one or more DNA fragments in a first PCR-reaction, preferably multiplex PCR or multiple PCR reactions in parallel, using a first set of amplicon specific primers, each of the primers comprising an adaptor, preferably one adaptor for the forward primer and another adaptor for the reverse primer, and (b) subsequently amplifying the one or more DNA fragments in a second PCR reaction using a second set of primers directed against the adaptor sequences, wherein either or both of the second set of primers comprises a DNA-tag;
  (ii) documenting the relation between the introduced DNA tag and the sample from which the one or more DNA fragments are derived;
  (iii) determining the nucleic acid sequence of the DNA fragment in order to characterise the part of the fragment derived from the sample and to determine the origin of the DNA fragment using the information collected in step (ii).

In a preferred embodiment, a method is provided for the simultaneous sequencing of multiple DNA fragments derived from different samples comprising the steps of:
  i. introducing a DNA tag into the respective DNA fragments derived from the respective genetic samples comprising (a) the amplification of the DNA fragments in a first PCR-reaction, preferably multiplex PCR or multiple PCR reactions in parallel, using a first set of amplicon specific primers, each of the primers comprising an adaptor, preferably one adaptor for the forward primer and another adaptor for the reverse primer, and (b) subsequently amplifying the DNA fragments in a second PCR reaction using a second set of primers directed against the adaptor sequences, wherein either or both of the second set of primers comprises a DNA-tag wherein the introduced DNA tags differ in between the different genetic samples;
  ii. documenting the relation between each of the introduced DNA tags and the respective samples from which the DNA fragments are derived;
  iii. pooling the respective DNA fragments
  iv. simultaneously determining the nucleic acid sequence of the DNA fragments in order to characterise the parts of the fragments derived from the samples and to determine the origin of each of the fragments using the information of step (ii).

At the end of a sequence reaction, a 3'-tag sequence may be difficult to determine. Indeed, lower resolutions of sequencing signals are obtained the more one progresses in the sequencing reaction, or because of the increase in background signal the more one progresses in the sequencing reaction. Loss of synchronization during the sequencing reaction results in an increasing background so that the actual sequence cannot be further read-out the more the sequencing reaction progresses. E.g., each step in a sequencing reaction will not be 100% efficient, so that a small fraction of an 'amplicon-clone' is not elongated, but will be elongated in the next step of the sequencing reaction, and will thus result in background signal. These background signals will accumulate as the sequencing reaction progresses. Therefore, a 3'-tag might be difficult to determine. This problem could be overcome by reducing the length of the amplicons to be sequenced, however this might not be an option since less sequence information will be obtained per amplicon. The use of poly-homo-stretch-tags could overcome this problem. In a poly-homo-stretch-tag, each letter of the code is not one nucleotide, but a stretch of 2 or more identical nucleotides. The sequence of the tag will therefore generate more intense signals, e.g. in a pyrosequencing reaction, so that it can be more easy discriminated from the background, and therefore allow that most sequence of the amplicon is used for characterization of the fragment under investigation.

Any process is prone to errors, especially at moments when contents of tubes are transferred to other tubes. The workflow of a sample for genetic testing involves many manipulations from different people, increasing the risk for potential errors, such as sample switching, contamination, wrong association of patient name and test result in genetic test report, etc. (FIG. 8). Especially in diagnostics this cannot be tolerated.

One way to overcome this is by molecular bar coding of the sample itself, i.e. in the sample, as is illustrated here. This way, each sample is uniquely "named". In this way the whole process is quality assured from the moment the molecular barcode is added (FIG. 9). Preferably that molecular bar code (in the present invention also defined as one or more marker nucleic acids) is added to the sample as early as possible. The earliest possible moment would be when the specimen for analysis is collected, e.g. the molecular bar code (one or more marker nucleic acids) is already present in the collector tube (e.g. collecting tube for a blood sample). The present invention also provides a vessel or collector tube wherein one or more marker nucleic acids are present, each such marker nucleic acid comprising a known nucleic acid sequence, the known sequence being unique for each of the added marker nucleic acids. However, in case more than one marker nucleic acids are added, at least one should be different, so that the set or combination of marker nucleic acids are unique for each sample. In such tubes or vessels other chemicals might be present, such as EDTA, for easy processing of the samples. Collector tubes that contain these molecular markers will then be used for collecting a biological sample (e.g. blood, saliva) that will feed in a test protocol.

The molecular bar code should be found at the end of the complete process, and this guarantees quality assurance.

Molecular bar coding is feasible in assays that analyze individual molecules and that analyze a large number of molecules so that a small proportion of all tested single molecules can be used for identification of the molecular bar code and therefore monitor the sample.

A molecular bar code could be a unique DNA fragment, for each sample under investigation one unique DNA fragment or a unique set of DNA fragments. This unique DNA fragment is flanked with adaptors (FIG. 10), so that it can processed together in the same strategy as all other fragments under investigation, so that the unique DNA barcode fragment proceeds through the whole process in an analogous strategy as the actual fragments of the sample under investigation. E.g. a first primer against such adapter sequence will allow amplification of the molecular bar code region in later steps. The adapter sequence is positioned so that PCR products of a reasonable length will be obtained in these later steps. The molecular bar code therefore needs the same features as the molecules under investigation, so that they can be processed simultaneously. It might be a synthetic molecule, or a plasmid, or even a recombinant bacteria containing such a plasmid. During the process they may be free in solution (e.g. blood) or bound to certain components of the sample solution (e.g. blood cells).

Such molecular bar code molecules can be easily generated by mutagenesis using oligonucleotides that contain random nucleotide stretches. The repertoire of molecular bar code molecules could be even expanded if random sequences are inserted at two positions, rather than at one position in a vector library (FIG. 10).

A 5 nucleotide molecular bar code allows 1024 different unique molecular bar code molecules. A 10 nucleotide molecular bar code allows about 1000000 unique different molecular bar code molecules, and so on. The synthesis of such a high number molecular bar code molecules is, however, quiet costly.

A more economic favorable way would be the use of more than 1 molecular bar code molecule to mark a sample, e.g. 3 molecular bar code molecules, all of them having the same adaptors to allow processing with the samples under investigation (FIG. 11). Especially in combination with a sample tag as described above, when 3 molecular bar codes are used, one would only need 30 molecular bar code molecules to obtained 1000 unique different combinations, compared to 1000 bar code molecules that would be needed if only one bar code molecule was used per sample. The combination with a sample tag will provide an extra control of the process, especially if they become covalently linked, since the correct combination of molecular bar code and sample tag should be found at the end of the process which ensures that complete process is quality-assured (FIGS. 6a, 6b, 9). Mixing of three type of molecular bar code molecules, in which the molecular bar code is coded by 5 nucleotides, i.e. 3072 (1024*3) molecular bar code molecules, allows more than $10^9$ ($1024^3$) different combinations of unique molecular bar codes, and allows many strategies of tagging (e.g. sample specific, sample-specific and lab-specific, . . . ) (FIG. 11). The molecular bar coding format can be used for different types of parallel sequencing techniques. The molecular bar code should be found at the end of the complete process, and this guarantees quality assurance (FIGS. 12 and 13).

Therefore, in yet another object of the present invention a method is provided for marking and subsequently verifying the origin and/or identity of a biological sample the method comprising the steps of (i) providing an isolated biological sample;

(ii) adding to the sample one or more marker nucleic acids, each such marker nucleic acid comprising a known nucleic acid sequence, the known sequence being unique for each of the added marker nucleic acids. However, in case more than one marker nucleic acid is added, at least one should be different for each sample;

(iii) documenting the relation between the identity and/or origin of the biological sample and the addition of the one or more marker nucleic acids to the sample;

(iv) detecting the presence in the biological sample the known nucleic acid sequences comprised in the marker nucleic acids;

(v) verifying whether the sequences detected in step (iv) are in accordance with the documentation obtained in step (iii) in order to verify the identity and/or origin of the biological sample.

Another embodiment of the present invention relates to a method for marking and subsequently verifying the origin and/or identity of a biological sample, comprising the steps of (i) providing a collector tube in which one or more marker nucleic acids, each such marker nucleic acid comprising a known nucleic acid sequence, the known sequence being unique for each of the added marker nucleic acids. However, in case more than one marker nucleic acid is added, at least one should be different for each sample; (ii) collecting a biological sample in the collector tube, (iii) documenting the relation between the identity and/or origin of the biological sample and the addition of the one or more marker nucleic acids to the sample; (iv) detecting the presence in the biological sample the known nucleic acid sequences comprised in the marker nucleic acids; (v) verifying whether the sequences detected in step (iv) are in accordance with the documentation obtained in step (iii) in order to verify the identity and/or origin of the biological sample.

Preferably, the presence in the biological sample of the known nucleic acid sequences is detected by PCR amplification of the sequences and subsequently sequencing the amplification products. Thus, a preferred embodiment of the present invention provides for a method for marking and subsequently verifying the origin and/or identity of a biological sample the method comprising the steps of
  (i) providing an isolated biological sample;
  (ii) adding to the sample one or more marker nucleic acids, each such marker nucleic acid comprising a known nucleic acid sequence, the known sequence being unique for each of the added marker nucleic acids. However, in case more than one marker nucleic acid is added, at least one should be different for each sample;
  (iii) documenting the relation between the identity and/or origin of the biological sample and the addition of the one or more marker nucleic acids to the sample;
  (iv) the amplification of one or more DNA fragments originating from the sample and amplification of the one or more marker nucleic acids in a multiplex or multiplex-like PCR-reaction using a first set of amplicon specific primers, wherein each forward primer of the set of amplicon specific primers comprises a same adaptor and wherein each reverse primer of the set of amplicon specific primers comprises a same adaptor;
  (v) subsequently amplifying the amplified nucleic acids of (iv) in a second PCR reaction using a second set of primers directed against the adaptor sequences, wherein either or both of the second set of primers comprises a sample specific DNA-tag.
  (vi) documenting the relation between the identity and/or origin of the biological sample and the addition of the sample specific DNA tag
  (vii) detecting the presence in the biological sample of the known nucleic acid sequences comprised in the marker nucleic acids and DNA tag, which preferably become covalently linked in step (v), preferably by simultaneously sequencing the amplified nucleic acids (both derived from the sample DNA fragments and the marker nucleic acids);
  (vii) verifying whether the sequences detected in step (vii) are in accordance with the documentation obtained in step (iii) and step (vi) in order to verify the identity and/or origin of the biological sample.

In the context of the present invention, multiplex-like PCR refer to multiple single PCR reactions occurring in parallel, such as e.g. in emulsion droplets or in integrated fluidic circuit technology.

Apart from the quality-assurance, such molecular bar codes allow automation of the laboratory and reporting protocols (FIG. 14).

Not only can these molecular bar codes be used in a DNA assay, in which the molecular bar code and sample are characterized in the same assay. Molecular DNA bar codes may be also used for any assay, in which the molecular DNA bar code typing and actual assay or two different assays (e.g. determination of protein in doping tests, and so on). In this way any sample, especially solution samples, can be labeled. Moreover, the labeling can be completely anonymous, so that willing incorrect manipulation can be hardly done.

Example 1

Amplicon-Specific KNEX-DNA-Crystal Multiplex Amplification of Fragments that Cannot be Co-Amplified in a Multiplex PCR Reaction If KNEX-DNA-crystals facilitate amplification in a multiplex amplification through keeping the amplicon-specific primers physically restricted, one would expect that amplicons which cannot be co-amplified in a standard multiplex PCR reaction should be co-amplified in amplicon-specific KNEX-DNA-crystal multiplex PCR reactions. If so, this could indicate a proof-of-principle of an amplicon-specific KNEX-DNA-crystal multiplex PCR assay.

In the past it was found that a 538 bp-amplicon containing exon 1 (FIG. 15) (lane 7), and a 341 bp-amplicon containing exon 3 (lane 8), of the SCNN1A gene, cannot be co-amplified in a standard multiplex PCR reaction. In the standard co-amplification reaction, the 341 bp-amplicon fails to amplify when both are combined (lane 9). In amplicon-specific KNEX-DNA-crystal multiplex PCR, in which amplicon-specific KNEX-DNA-crystals were build using 5 pmol of a double-biotinylated, 34 nucleotide long oligonucleotide (5'-B-CCGTTAACCCGATATCGGCCCGGGCCTTTAAACC-B-3' (biotin groups are underlined); in the presence of 2.5 pmol (lanes 1 and 4), 5 pmol (lanes 2 and 5), and 7.5 pmol (lanes 3 and 6) amplicon-specific primers; either in the presence of 1.25 pmol (lanes 1-3) or 2.5 pmol (lanes 4-6) streptavidin, the 341-bp-amplicon is amplified to variable degrees, of which the best result is obtained in lane 4. The fact that still individual amplicons can be visualized by electrophoresis, instead of DNA-smears because of aggregates of KNEX-DNA-crystals, indicates that not all amplicon-specific primers are aggregated in KNEX-DNA-crystals in this experiment or that streptavidin-biotin bounds were broken during the process. Lane D contains a 100 bp DNA ladder.

Example 2

Sequencing

Parallel pyrosequencing in high-density picoliter reactors by the Genome Sequencer (454 Life Sciences Inc, Roche Applied Science) allows the determination of millions of nucleotides in a single run hours (2).

In such sequencing assays, total genomic DNA is randomly fragmented to 25-500 bp fragments, depending on the sequencing technology, to which adapters are ligated. Amplification is then performed with two universal primers against these adaptors so that all fragments are amplified simultaneously. For resequencing purposes of a gene, this 'universal' amplification step with two primers cannot be performed, since each amplicon needs to be amplified by its own specific pair of two primers. Moreover, since the coding region of genes can be more than 5 kb, many amplicons need to be amplified.

Multiplex amplification of all these amplicons in a single, or a limited number of, PCR reaction(s) would thus render amplicon-sequencing more convenient and cheaper. This may be achieved by amplicon-specific KNEX-DNA-crystal multiplex PCR as described above. In combination with sample tags, different samples can be pooled (FIG. 4b) and in combination with molecular bar codes the complete process can be quality-assured (FIG. 5a).

Example 3

Determination of Large Genomic Deletions, Insertions or Duplications

Some mutations might result in complete loss, duplication or insertion of larger DNA fragments. Such fragments may encompass 1 or more complete exons of a gene. Such mutations are missed in mutation scanning assays (e.g. sequencing) of the complete coding region, and the exon/intron junctions, of a gene. Indeed, such assays make use of PCR products obtained in the plateau phase of a PCR reaction. In case of an individual, having a recessive disease and who is heterozygous for a complete deletion of 1 exon, the corresponding region in the other gene will still be amplified, and in case that the mutation in that other gene is located outside that exon, a normal sequence will be read. It will then be concluded that the individual carries the wild type nucleotides on both genes, while in fact the sequence was read from 1 gene only. Techniques such as MLPA (multiplex ligation probe mediated amplification) or QMPSF (Quantitative Multiplex PCR of Short fluorescent Fragments) allow the detection of the complete loss or duplication of exons. These quantitative techniques are based on multiplex amplification and therefore have their limitations in robustness and accuracy. Since that these assays are based on quantitative principles, preferential amplification of smaller fragments may lead to false conclusions or results that cannot be analyzed. Amplicon-specific KNEX-DNA-crystal multiplex PCR amplifications may thus result in more robust quantitative multiplex amplification, MLPA, or QMPSF assays. In case that amplicon-specific KNEX-DNA-crystal multiplex PCR amplification is quantitative, such deletions or insertions may be even detected in sequencing technologies that perform parallel sequencing starting from single template molecules. Indeed, in these sequencing technologies each amplicon is sequenced at a certain coverage or redundancy. If a higher or lower amount of sequenced amplicons are detected in a multiplex of amplicons, the deletion or duplication of that amplicon may then be concluded. Especially since most deletions/duplications will be covered by more than 1 amplicon, different amplicons are in fact controls for each other. These parallel sequencing assays may then also provide quantitative information besides qualitative sequence determination. Analogously, more complex copy number variations (CNVs) can be determined.

REFERENCES (1) Hamady, M. et al (2008) Error-correcting barcoded primers for pyrosequencing hundreds of samples in multiplex. *Nat Methods*, 5, 235-7.
(2) Margulies, M. et al. et al. (2005) Genome sequencing in microfabricated high-density picolitre reactors. *Nature*, 437, 376-80.

What is claimed is:

1. A method for introducing a sample specific DNA tag into a plurality of DNA fragments from a plurality of samples comprising genetic material, said method comprising, for each of the samples, the steps of:
  (i) amplifying DNA fragments in a first multiplex or multiplex-like PCR reaction using amplicon specific forward and reverse primers, wherein each forward amplicon specific primer comprises a first adaptor sequence and wherein each reverse amplicon specific primer comprises a second adaptor, wherein the first adaptor sequence is identical in all forward primers for each of the samples and wherein the second adaptor sequence is identical in all reverse primers for each of the samples,
  (ii) further amplifying the amplified nucleic acids obtained in step (i), using one set of forward and reverse sample specific primers which are directed against said first and second adaptor sequences, wherein one or both of said sample specific primers comprises a DNA sequence which differs for each of the samples.

2. The method according to claim 1, wherein one or both of said sample specific primers comprise(s) one or more additional different adaptors for further processing purposes.

3. The method according to claim 1, wherein the amplicon specific primers used in step (i) and the sample specific primers used in step (ii) are added together in one reaction mixture.

4. The method according to claim 3, wherein the amplicon specific primers and the sample specific primers have specific different melting temperatures allowing selective amplification by modifying the annealing temperature.

5. The method according to claim 1, further comprising the steps of:
   (iii) determining for an amplified DNA fragment obtained in step (ii) the nucleic acid sequence of the sample specific DNA tag and the nucleic acid sequence of the DNA fragment, and
   (iv) correlating the sequence information of said DNA fragment with the sample from which said DNA fragment is derived.

6. The method according to claim 5, wherein the amplified nucleic acids are pooled prior to determining the nucleic acid sequence of said amplified nucleic acids.

7. The method according to claim 1, further comprising prior to step (i), the step of adding to each sample one or a combination of different marker nucleic acids, with a known nucleic acid sequence,
   wherein for each sample, the marker nucleic acid, or the combination of different marker nucleic acid is unique, and
   wherein said marker sequence or sequences are amplified with amplicon specific markers and sample specific markers in accordance with step (i) and (ii).

8. The method according to claim 7, further comprising the step of, after amplification of a marker nucleic acid, determining the sequence of the sample specific DNA tag and the sample specific DNA marker sequence in said amplified DNA marker nucleic acid.

9. The method according to claim 7, wherein each of the different nucleic acids in a combination of marker nucleic acids comprises a randomly generated molecular bar code region and wherein each of the different nucleic acids comprises 5' and/or 3' of the randomly generated molecular bar code region an adapter sequence which is identical for each of the different marker nucleic acids and which is able to anneal with a primer allowing for the amplification of the molecular bar code region.

10. The method according to claim 7, wherein said added marker nucleic acids are designed so that they can be processed together or in parallel in the same strategy as the nucleic acid sequences of the biological sample under investigation.

11. The method according to claim 7, wherein the one or more marker nucleic acids are present in a collector tube prior to the administration of a sample.

* * * * *